(12) United States Patent
Kim et al.

(10) Patent No.: US 10,987,386 B2
(45) Date of Patent: Apr. 27, 2021

(54) **METHOD FOR TREATING INFLAMMATION OR CANCER USING EXTRACELLULAR VESICLES DERIVED FROM *LACTOBACILLUS PARACASEI***

(71) Applicant: MD HEALTHCARE INC., Seoul (KR)

(72) Inventors: Yoon-Keun Kim, Paju-Si (KR); Chang Mo Moon, Seoul (KR)

(73) Assignee: MD HEALTHCARE INC., Seoul (KR)

(*) Notice: Subject to any disclaimer, the term of this patent is extended or adjusted under 35 U.S.C. 154(b) by 0 days.

(21) Appl. No.: 16/782,288

(22) Filed: Feb. 5, 2020

(65) Prior Publication Data
US 2020/0206282 A1  Jul. 2, 2020

Related U.S. Application Data

(63) Continuation of application No. PCT/KR2019/010267, filed on Aug. 13, 2019.

(30) Foreign Application Priority Data

Dec. 31, 2018 (KR) .................. 10-2018-0174027
Apr. 25, 2019 (KR) .................. 10-2019-0048671

(51) Int. Cl.
*A61K 35/742* (2015.01)
*A61P 29/00* (2006.01)
*A61P 35/00* (2006.01)
*A61K 9/00* (2006.01)

(52) U.S. Cl.
CPC ............ *A61K 35/742* (2013.01); *A61K 9/007* (2013.01); *A61P 29/00* (2018.01); *A61P 35/00* (2018.01)

(58) Field of Classification Search
None
See application file for complete search history.

(56) References Cited

U.S. PATENT DOCUMENTS 10,406,184 B2 * 9/2019 Kim .................. A61K 8/99

FOREIGN PATENT DOCUMENTS

| KR | 10-2011-0052808 A | | 5/2011 |
| KR | 10-2016-0008060 A | | 1/2016 |
| KR | 10-2019-0048671 | * | 4/2020 |

OTHER PUBLICATIONS

Aoki-Yoshida, A. et al. Exosomes Isolated from Sera of Mice Fed Lactobacillus Strains Affect Inflammatory Cytokine Production in Macrophages In vitro. Biochemical and Biophysical Research Communications 489:248-254, May 2017. (Year: 2017).*
Steinbichler T. et al. The Role of Exosomes in Cancer Metastasis. Seminars in Cancer Biology 44:170-181, Feb. 2017. (Year: 2017).*

* cited by examiner

*Primary Examiner* — Ralph J Gitomer
(74) *Attorney, Agent, or Firm* — Vorys, Sater, Seymour & Pease LLP; Mih Suhn Koh

(57) ABSTRACT

The present invention relates to an extracellular vesicle derived from *Lactobacillus paracasei* and a use thereof, and more particularly, to a composition for alleviating, preventing or treating an inflammation disease and a cancer, which comprises an extracellular vesicle derived from *Lactobacillus paracasei*, which may effectively inhibit various inflammation disease, as an active ingredient, and the like.

8 Claims, 21 Drawing Sheets
Specification includes a Sequence Listing.

METHOD FOR TREATING INFLAMMATION OR CANCER USING EXTRACELLULAR VESICLES DERIVED FROM *LACTOBACILLUS PARACASEI*

CROSS-REFERENCE TO RELATED APPLICATIONS

This application is a Continuation of PCT/KR2019/010267, filed Aug. 13, 2019, which claims the benefit of priority from Korean Patent Application No. 10-2018-0174027, filed Dec. 31, 2018 and Korean Patent Application No. 10-2019-0048671, filed Apr. 25, 2019, the contents of each of which are incorporated herein by reference in its entirety.

SEQUENCE LISTING

The Sequence Listing submitted in text format (.txt) filed on Feb. 5, 2020, named "SequenceListing.txt", created on Nov. 21, 2019 (3.10 KB), is incorporated herein by reference.

TECHNICAL FIELD

The present invention relates to an extracellular vesicle derived from *Lactobacillus paracasei* and a use thereof, and more particularly, to a composition for preventing or treating an inflammation disease and a cancer, which comprises an extracellular vesicle derived from *Lactobacillus paracasei* as an active ingredient, and the like.

This application claims priority to and the benefit of Korean Patent Application Nos. 10-2018-0174027 and 10-2019-0048671 filed in the Korean Intellectual Property Office on Dec. 31, 2018 and Apr. 25, 2019, respectively, and all the contents disclosed in the specification and drawings of the applications are incorporated in this application.

BACKGROUND ART

As the 21st century begins, the importance of an acute infectious disease that used to be recognized as a communicable disease in the past has decreased, whereas the pattern of diseases has changed as a major disease that reduces the quality of life and determines the human's life expectancy due to chronic diseases. The chronic disease is characterized by a chronic inflammation accompanied by abnormalities of immune function, and diseases such as various chronic inflammation diseases and cancers that are caused by these diseases have become a major problem in national health.

Inflammation is a local or systemic protective mechanism against the damage or infection of cells and tissues, and is typically caused by serial biological responses occurring as humoral mediators that constitute the immune system directly response to the damage or infection or stimulate the local or systemic effector system. Examples of a main inflammatory disease include digestive diseases such as gastritis and inflammatory enteritis, oral diseases such as periodontitis, respiratory diseases such as asthma, chronic obstructive pulmonary disease (COPD), and rhinitis, dermatological diseases such as atopic dermatitis, alopecia, and psoriasis, arthritis such as degenerative arthritis and rheumatoid arthritis, cancers, and the like.

Common compositions used to treat or prevent chronic inflammation diseases are largely classified into steroidal and non-steroidal compositions, most of which are often accompanied by various side effects in many cases. Therefore, there is a trend in which interests in a TNF-α inhibitor, which is a pro-inflammatory cytokine known to be a main cause of chronic inflammation diseases, have been recently increased.

However, the development of drugs that have low side effects and may be substantially used for the prevention and treatment of chronic inflammation diseases by effectively suppressing the expression of TNF-α still has been inadequate to date, and the same applies to cancer therapeutic agents.

DISCLOSURE

Technical Problem

The present invention has been devised to solve the aforementioned problems in the related art, and an objective thereof is to provide a composition for alleviating, preventing or treating an inflammation disease and a cancer, which comprises an extracellular vesicle derived from *Lactobacillus paracasei* as an active ingredient, and the like.

However, a technical problem to be achieved by the present invention is not limited to the aforementioned problems, and the other problems that are not mentioned may be clearly understood by a person skilled in the art from the following description.

Technical Solution

The present invention provides a pharmaceutical composition for preventing or treating an inflammation disease or a cancer, which comprises an extracellular vesicle derived from *Lactobacillus paracasei* as an active ingredient.

In addition, the present invention provides a food composition for preventing or alleviating an inflammation disease or a cancer, which comprises an extracellular vesicle derived from *Lactobacillus paracasei* as an active ingredient.

In addition, the present invention provides a inhalant composition for preventing or treating an inflammation disease or a cancer, which comprises an extracellular vesicle derived from *Lactobacillus paracasei* as an active ingredient.

In addition, the present invention provides a cosmetic composition for preventing or alleviating an inflammation disease, which comprises an extracellular vesicle derived from *Lactobacillus paracasei* as an active ingredient.

The inflammation disease of the present invention is a disease mediated by TNF-α or IL-1β, and comprises an inflammatory enteritis (acute enteritis, chronic enteritis, and the like), gastritis, asthma, chronic obstructive pulmonary disease (COPD), rhinitis, atopic dermatitis, alopecia, psoriasis, degenerative arthritis, and rheumatoid arthritis, but is not limited thereto as long as the inflammation disease is a disease caused by an inflammatory response.

The cancer of the present invention comprises colorectal cancer, gastric cancer, lung cancer, liver cancer, bile duct cancer, pancreatic cancer, breast cancer, ovarian cancer, renal cancer, bladder cancer, and prostate cancer, but is not limited thereto.

In an embodiment of the present invention, the extracellular vesicle has an average diameter of preferably 10 to 300 nm, but is not limited thereto as long as the extracellular vesicle is an extracellular vesicle that is naturally or artificially secreted or isolated from *Lactobacillus paracasei*.

In another embodiment of the present invention, the extracellular vesicle may be isolated from a culture solution of *Lactobacillus paracasei*, or a food product cultured by adding *Lactobacillus paracasei*, but is not limited thereto.

In addition, the present invention provides a method of treating an inflammation disease or a cancer, the method comprising a step of administering a composition comprising an extracellular vesicle derived from *Lactobacillus paracasei* as an active ingredient to a subject.

Further, the present invention provides a use of a composition for preventing and/or treating an inflammation disease or a cancer, which comprises an extracellular vesicle derived from *Lactobacillus paracasei* as an active ingredient.

In addition, the present invention provides a use of an extracellular vesicle derived from *Lactobacillus paracasei* for producing a drug used against an inflammation disease and/or a cancer.

Advantageous Effects

Since the extracellular vesicle derived from *Lactobacillus paracasei* according to the present invention may effectively suppress the expression of TNF-α, IL-1β, and the like which are pro-inflammatory cytokines known to be factors of various chronic inflammation diseases, it is expected that the extracellular vesicle derived from *Lactobacillus paracasei* according to the present invention can be broadly used as an agent for alleviating, preventing, or treating various chronic inflammation diseases and cancers having low side effects.

MODES OF THE INVENTION

Figure 1A:
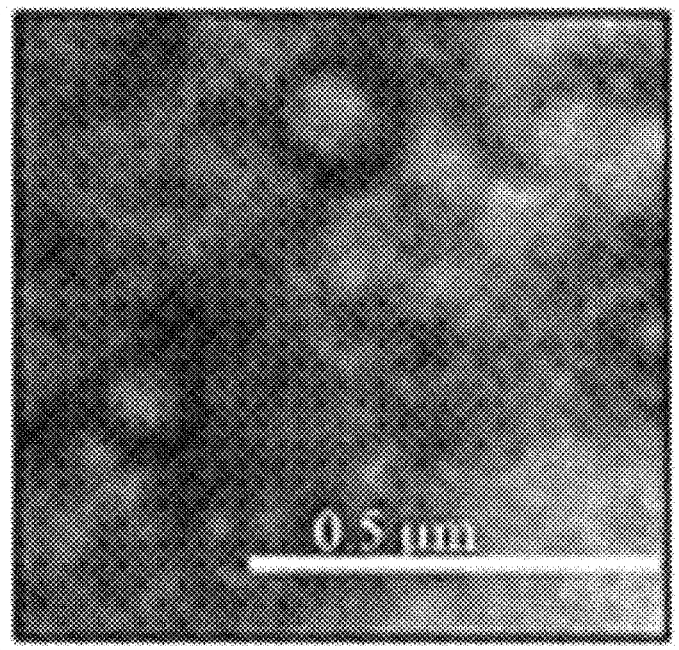
FIGS. 1A and 1B are views illustrating the results of analyzing the extracellular vesicle derived from *Lactobacillus paracasei* according to an example of the present invention.

In the present invention, it was confirmed that the extracellular vesicle derived from *Lactobacillus paracasei* exhibited a remarkable therapeutic effect on inflammation diseases by effectively suppressing the expression of various factors associated with inflammatory responses. Accordingly, it is expected that the extracellular vesicle derived from *Lactobacillus paracasei* of the present invention may be variously used for alleviating, preventing, and treating various chronic inflammation diseases and cancers.

As used herein, the "extracellular vesicle" refers to a structure formed of a nano-sized membrane and secreted from various bacteria, and in the present invention, the "extracellular vesicle" collectively refers to all structures formed of a membrane and naturally secreted or artificially produced from *Lactobacillus paracasei*. The extracellular vesicles may be isolated from a culturing solution comprising *Lactobacillus paracasei* bacterial cell by using one or more methods selected from the group consisting of centrifugation, ultra-high speed centrifugation, high pressure treatment, extrusion, sonication, cell lysis, homogenization, freezing-thawing, electroporation, mechanical decomposition, chemical treatment, filtration by a filter, gel filtration chromatography, free-flow electrophoresis, and capillary electrophoresis. Further, a process such as washing for removing impurities and concentration of obtained vesicles may be further included.

As used herein, the "inflammation disease" refers to a disease caused by in vivo inflammatory responses, and representative examples thereof comprise: respiratory inflammation diseases such as asthma, chronic obstructive pulmonary disease, and rhinitis; dermatological inflammation diseases such as atopic dermatitis, psoriasis, acne, contact dermatitis, and alopecia; digestive tract inflammation diseases such as gastritis, gastric tract ulcer, and inflammatory enteritis (acute enteritis, Crohn's disease, inflammatory bowel disease, Behcet's colitis, ulcerative colitis, bacterial enteritis, and the like); vaginitis; arthritis such as osteoarthritis and rheumatoid arthritis; complications thereof; and the like. Further, the inflammatory disease is used with a meaning comprising, in addition to general inflammatory diseases, metabolic diseases related to inflammatory responses, examples of which comprise diabetes, obesity, hepatitis, hepatic sclerosis, and the like.

As used herein, the "prevention" refers to all actions that suppress the inflammation disease and cancer or delay the onset thereof via administration of the food, cosmetic, inhalant, or pharmaceutical composition according to the present invention.

As used herein, the "treatment" refers to all actions that alleviate or beneficially change symptoms of the inflammation disease and cancer via administration of the food, cosmetic, inhalant, or pharmaceutical composition according to the present invention.

As used herein, the "alleviation" refers to all actions that at least reduce a parameter associated with a condition to be treated, for example, the degree of symptoms.

As used herein, the "individual" refers to a subject in need of treatment of a disease, and more specifically, refers to a mammal such as a human or a non-human primate, a mouse, a rat, a dog, a cat, a horse, and a cow.

As used herein, the "pharmaceutical composition" may be in the form of a capsule, a tablet, a granule, an injection, an ointment, a powder, or a beverage, and the pharmaceutical composition may be targeting humans. Each pharmaceutical composition may be formulated into the form of an oral dosage form such as a powder, a granule, a capsule, a tablet, or an aqueous suspension, an external preparation, a suppository, or a sterile injectable solution, but the formulation thereof is not limited thereto. The pharmaceutical composition of the present invention may comprise a pharmaceutically acceptable carrier. As the pharmaceutically acceptable carrier, a binder, a lubricant, a disintegrant, an excipient, a solubilizing agent, a dispersing agent, a stabilizer, a suspending agent, a colorant, a flavoring agent, and the like may be used for oral administration, a mixture of a buffering agent, a preservative, an analgesic, a solubilizer, an isotonic agent, a stabilizer, and the like may be used for injection, and a base, an excipient, a lubricant, a preservative, and the like may be used for topical administration. The formulation of the pharmaceutical composition of the present invention may be variously prepared by mixing the pharmaceutical composition of the present invention with the pharmaceutically acceptable carrier as described above. For example, the formulation may be prepared in the form of a tablet, a troche, a capsule, an elixir, a suspension, a syrup, a wafer, and the like for oral administration, and as unit dosage ampoules or multiple dosage forms for injection. The pharmaceutical composition of the present invention may also be formulated into solutions, suspensions, tablets, capsules, sustained-release preparations, and the like.

Meanwhile, as an example of suitable carriers, excipients and diluents for formulation, it is possible to use lactose, dextrose, sucrose, sorbitol, mannitol, xylitol, erythritol, maltitol, starch, acacia rubber, alginate, gelatin, calcium phosphate, calcium silicate, cellulose, methylcellulose, microcrystalline cellulose, polyvinylpyrrolidone, water, methylhydroxybenzoate, propylhydroxybenzoate, talc, magnesium stearate, mineral oil, or the like. Further, the pharmaceutical composition of the present invention may further include a filler, an anticoagulant, a lubricant, a wetting agent, a flavoring agent, an emulsifying agent, a preservative, and the like.

The route of administration of the pharmaceutical composition according to the present invention comprises, but is not limited to, oral, intravenous, intramuscular, intraarterial, intramedullary, intradural, intracardiac, transdermal, subcutaneous, intraperitoneal, intranasal, intestinal, topical, sublingual, and rectal routes. Oral or parenteral administration is preferred. As used herein, the term "parenteral" has a meaning that includes subcutaneous, intradermal, intravenous, intramuscular, intraarticular, intrasynovial, intrasternal, intradural, intralesional and intracranial injection or infusion techniques. The pharmaceutical composition of the present invention may also be administered in the form of a suppository for rectal administration.

The pharmaceutical composition of the present invention may vary depending on various factors including the activity of the specific compounds used, age, body weight, general health, sex, diet, time of administration, route of administration, rate of excretion, drug combination and the severity of the particular disease to be prevented or treated, and the dosage of the pharmaceutical composition varies depending on the condition and body weight of the patient, the severity of disease, the form of drug, the route and duration of administration, but may be appropriately selected by a person skilled in the art, and may be 0.0001 to 50 mg/kg or 0.001 to 50 mg/kg daily. The administration may be carried out once daily, and may be divided into several times. The dosage is not intended to limit the scope of the present invention in any way. The pharmaceutical composition according to the present invention may be formulated into pills, sugar-coated tablets, capsules, solutions, gels, syrups, slurries, and suspensions.

In the present invention, the food composition may be used for various foods, for example, beverages, gums, teas, vitamin composites, health-supplementary foods, and may be used in the form of a pill, a powder, a granule, an infusion, a tablet, a capsule, or a beverage. The food composition comprises a health functional food composition. In this case, generally in the present invention, the amount of the extracellular vesicle derived from *Lactobacillus paracasei* used in a food or a beverage may be 0.01 to 15 wt % based on the weight of the entire food in the case of a food composition, and may be in a ratio of 0.02 to 10 g and preferably 0.3 to 1 g based on 100 mL in the case of a health beverage composition. As used herein, the health functional food is a food that is prepared and/or processed using a raw material or ingredient having a function useful for the human body, and refers to a food that has a unique feature in the ingredient thereof as compared to general foods, and has more positive health maintenance, or purpose or expected effects.

The food composition of the present invention may comprise a typical food additive in the art, for example, a flavoring agent, a savoring agent, a colorant, a filler, a stabilizer, and the like. The food composition according to the present invention is not particularly limited in an ingredient to be added as an essential ingredient in addition to the extracellular vesicle derived from *Lactobacillus paracasei*, and may contain various flavoring agents or natural carbohydrates, and the like as an additional ingredient. Examples of the above-described natural carbohydrate include common sugars such as monosaccharides, for example, glucose, fructose and the like; disaccharides, for example, maltose, sucrose and the like; and polysaccharides, for example, dextrin, cyclodextrin and the like, and sugar alcohols such as xylitol, sorbitol, and erythritol. As the flavorant other than those described above, a natural flavorant (thaumatin, stevia extract (for example, rebaudioside A, glycyrrhizin and the like), and a synthetic flavorant (saccharin, aspartame and the like) may be advantageously used. The proportion of the natural carbohydrate is generally about 1 to 20 g, and preferably about 5 to 12 g per 100 mL of the composition of the present invention.

The food composition of the present invention may contain various nutrients, vitamins, minerals (electrolytes), flavoring agents such as synthetic flavoring agents and natural flavoring agents, colorants and fillers (cheese, chocolate, and the like), pectic acid and salts thereof, alginic acid and salts thereof, organic acids, protective colloid thickeners, pH adjusting agents, stabilizers, preservatives, glycerin, alcohols, carbonating agents used in a carbonated beverage, or the like, in addition to the additives. These ingredients may be used either alone or in combinations thereof. The proportion of these additives is not of high significance, but is generally selected within a range of 0 to 20 parts by weight per 100 parts by weight of the composition of the present invention.

In the present invention, a cosmetic composition may contain the extracellular vesicle derived from *Lactobacillus paracasei* in an amount of 0.0005 to 50 wt % based on the total weight of the composition. Further, the composition of the present invention may further contain one or more active ingredients exhibiting the same or similar functions in addition to the extracellular vesicle derived from *Lactobacillus paracasei*.

A cosmetic prepared using the cosmetic composition of the present invention may be prepared in the form of a general emulsion formulation and a general solubilized formulation. Examples of a cosmetic of the emulsion formulation comprise nourishing lotion, cream, essence, and the like, and examples of a cosmetic of the solubilized formulation comprise a skin softener. In addition, by containing a dermatologically acceptable medium or base, the cosmetic may be prepared in the form of an auxiliary agent that may be topically or systemically applied and typically used in the dermatology field.

A suitable cosmetic formulation may be provided in the form of, for example, a solution, a gel, a solid or an anhydrous paste product, an emulsion, a suspension, a microemulsion, a microcapsule, a microgranule, or an ionic (liposome) and non-ionic vesicular dispersion, which is obtained by dispersing an oil phase in an aqueous phase, a cream, a skin toner, a lotion, a powder, an ointment, a spray, or a conceal stick. Furthermore, the cosmetic composition may be prepared in the form of a foam or an aerosol composition that further contains a compressed propellant.

Further, the pharmaceutical composition of the present invention may additionally contain auxiliary agents typically used in the cosmetology or dermatology field, such as a fatty substance, an organic solvent, a solubilizing agent, a thickener and a gelling agent, a softener, an antioxidant, a suspending agent, a stabilizer, a foaming agent, a fragrance, a surfactant, water, an ionic or a non-ionic emulsifier, a filler, a metal ion sequestering agent, a chelating agent, a preservative, a vitamin, a blocking agent, a wetting agent, an essential oil, a dye, a pigment, a hydrophilic or lipophilic active agent, a lipid vesicle, or any other ingredients typically used in a cosmetic. In addition, the ingredients may be introduced in an amount generally used in the dermatology field.

Examples of products to which the cosmetic composition of the present invention may be added include cosmetics such as astringents, skin softeners, nourishing toners, various creams, essences, packs, foundations, and the like, cleansings, face cleansers, soaps, treatments, beauty liquids, and the like.

Particular preparations of the cosmetic composition of the present invention include a skin lotion, a skin softener, a skin toner, an astringent, a lotion, a milk lotion, a moisturizing lotion, a nourishing lotion, a massage cream, a nourishing cream, a moisturizing cream, a hand cream, an essence, a nourishing essence, a pack, a soap, a shampoo, a cleansing foam, a cleansing lotion, a cleansing cream, a body lotion, a body cleanser, an emulsion, a press powder, a loose powder, an eye shadow, and the like.

In an inhalant composition of the present invention, the active ingredient may be directly added to an inhalant or may be used in combination with other ingredients, and may be appropriately used according to a general method. A mixing amount of the active ingredient may be appropriately determined according to the purpose of use thereof (for prevention or treatment).

In addition, the present invention provides a method of treating inflammation disease or a cancer, the method comprising a step of administering a composition comprising an extracellular vesicle derived from *Lactobacillus paracasei* as an active ingredient to a subject.

Further, the present invention provides a use of a pharmaceutical composition for preventing and/or treating an inflammation disease or a cancer, which comprises an extracellular vesicle derived from *Lactobacillus paracasei* as an active ingredient.

In addition, the present invention provides a use of an extracellular vesicle derived from *Lactobacillus paracasei* for producing a drug used against an inflammation disease or a cancer.

In the present invention, the "administration" refers to administration of the pharmaceutical composition of the present invention to a patient by any appropriate method, and for the route of administration of the composition of the present invention, the composition of the present invention may be administered via various oral or parenteral routes, as long as the composition of the present invention can reach a target tissue.

Hereinafter, preferred Examples for helping the understanding of the present invention will be suggested. However, the following Examples are provided only to more easily understand the present invention, and the contents of the present invention are not limited by the following Examples.

EXAMPLE

Example 1. Isolation of Extracellular Vesicle from *Lactobacillus paracasei*

In order to isolate an extracellular vesicle (EV) derived from *Lactobacillus paracasei*, *Lactobacillus paracasei* was inoculated into a de Man-Rogosa and Sharpe (MRS) medium, cultured at 37° C. and 200 rpm until the absorbance ($OD_{600nm}$) was 1.0 to 1.5, and then *Lactobacillus paracasei* was re-inoculated into a Luria Bertani (LB) medium and cultured. Then, a supernatant from which bacterial cells had been removed was obtained by recovering the culture solution including bacterial cells and performing centrifugation at 4° C. and 10,000 g for 20 minutes. The obtained supernatant was again filtered using a 0.22 μm filter, and the filtered supernatant was concentrated to a volume of 50 mL or less using a 100 kDa Pellicon 2 Cassette filter membrane (Merck Millipore) and a MasterFlex pump system (Cole-Parmer). An extracellular vesicle derived from *Lactobacillus paracasei* was isolated by filtering the concentrated supernatant again using a 0.22 μm filter. The amount of protein included in the supernatant was measured using a Pierce BCA Protein Assay kit (Thermo Fisher Scientific). Then, the isolated extracellular vesicle was observed using a JEM-1011 transmission electron microscope (TEM, JEOL) and a Zetasizer Nano ZS (Malvern Instruments). As a control, an extracellular vesicle derived from *Escherichia coli* was isolated by the same method. The results are illustrated in FIGS. 1A and 1B.

Figure 1B:
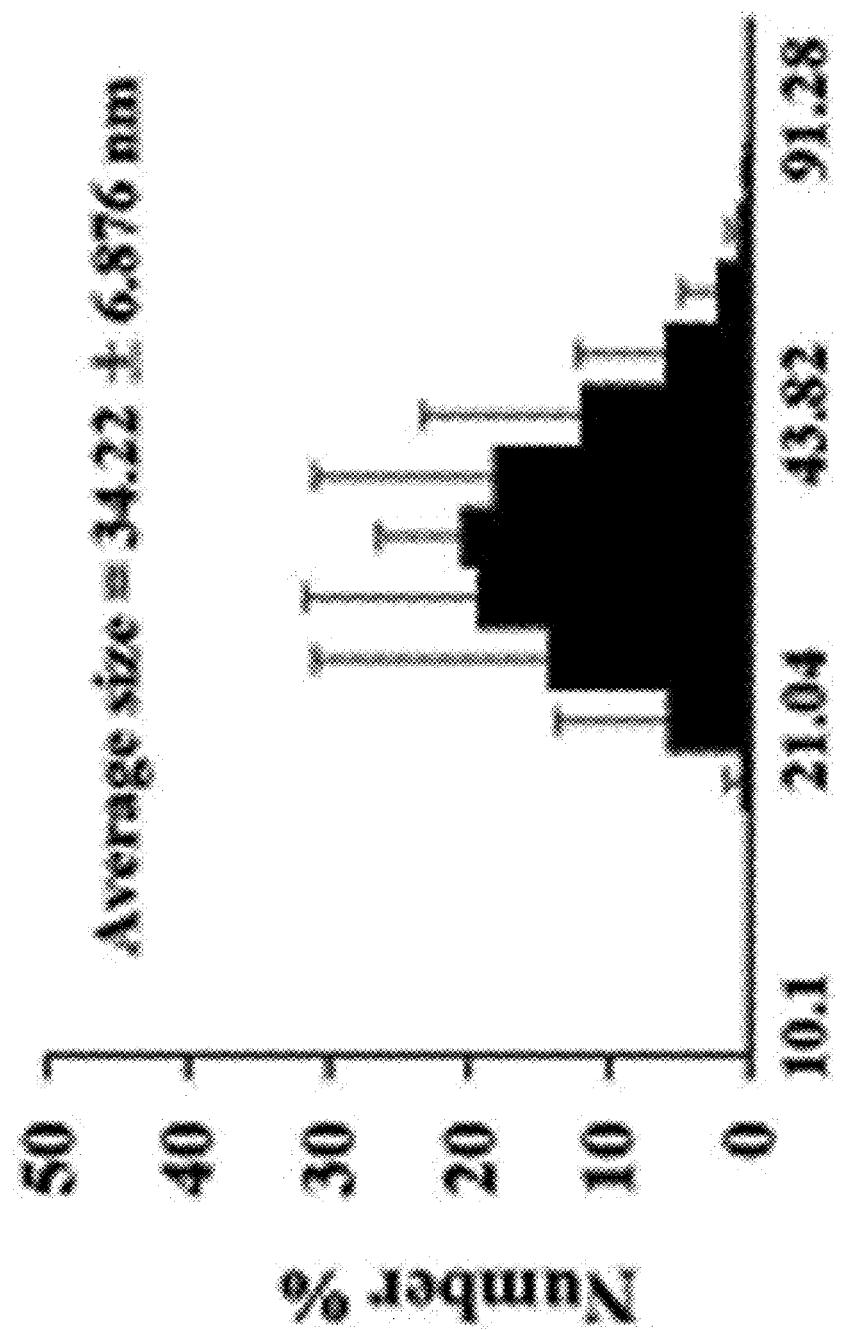

As illustrated in FIGS. 1A and 1B, it was confirmed that the extracellular vesicle isolated from the culture solution of *Lactobacillus paracasei* had an average diameter of 34.22 nm, and was normally isolated.

Example 2: Preparation of Bacterial Cells of *Lactobacillus paracasei*

In order to compare a extracellular vesicle derived from *Lactobacillus paracasei* with bacterial cells, *Lactobacillus paracasei* bacterial cells were prepared. More specifically, after the *Lactobacillus paracasei* bacterial cells cultured in the same manner as in Example 1 were heat-treated at 70°

C. for 1 hour, bacterial cells inactivated by heat, from which the supernatant had been removed by centrifugation at 4° C. and 10,000 g for 20 minutes, were obtained. Then, after the bacterial cells were re-floated again using a phosphate buffered saline (PBS), the amount of protein was measured using a Pierce BCA Protein Assay kit (Thermo Fisher Scientific).

Example 3. Confirmation of Inflammation-Inducing Effect of *Lactobacillus paracasei*-Derived Extracellular Vesicles In order to confirm the effects of the extracellular vesicle derived from *Lactobacillus paracasei* on the inflammation response in inflammatory cells, the extracellular vesicle derived from *Lactobacillus paracasei* was used to treat a mouse macrophage cell line Raw 264.7 at a concentration of 0.1, 1, and 10 μg/mL and allowed to react, and then the degree of cell apoptosis and the secretion amount of TNF-α were measured. More specifically, Raw 264.7 cells, which were dispensed into a 48-well cell culture plate at a density of 5×10 cells/well, were treated with *Lactobacillus paracasei*-derived vesicles in a Dulbecco's Modified Eagle's Medium (DMEM) serum-free medium and cultured for 12 hours. Then, the degree of cell apoptosis was measured using EZ-CYTOX (Dogen), the cell culture solution was put into a 1.5 mL tube, only a supernatant thereof was obtained by centrifugation at 3,000 g for 5 minutes, and then stored at −80° C., and ELISA was performed. For ELISA, a capture antibody was diluted with phosphate buffered saline (PBS) and 50 μl aliquots thereof were dispensed into a 96-well plate, and then allowed to react at 4° C. for 16 hours. Subsequently, the sample was washed three times with 100 μl of a PBST (0.05% Tween-20-containing PBS) solution, and then an RD (1% bovine serum albumin (BSA)-containing PBS) solution was dispensed in 100 μl aliquots per well, followed by blocking at room temperature for 1 hour. Then, a sample to be tested and a standard were adjusted to the same concentration, 50 μL of both samples were each added thereto, and the resulting solution was allowed to react at room temperature for 2 hours and washed three times using PBST. Then, the detection antibodies were diluted in RD, 50 μL of the resulting solution was added per well, allowed to react at room temperature for 2 hours, and washed three times using PBST to thoroughly remove unbound antibodies, and then 50 μL of Streptavidin-HRP (R&D system) diluted 1/40 in RD was added per well, and the resultant was allowed to react at room temperature for 20 minutes. Lastly, the sample and the standard were washed three times with 100 μl of PBST, and then a tetramethylbenzidine (TMB) substrate (SurModics, USA) was dispensed in 50 μl aliquots per well, and then when color was developed after 5 minutes to 20 minutes, a 1M sulfuric acid solution was dispensed in 50 μl aliquots per well, thereby stopping the reaction, and absorbance at 450 nm was measured using a SpectraMax M3 microplate reader (Molecular Devices). The results are illustrated in FIGS. 2A and 2B.

Figure 2A:
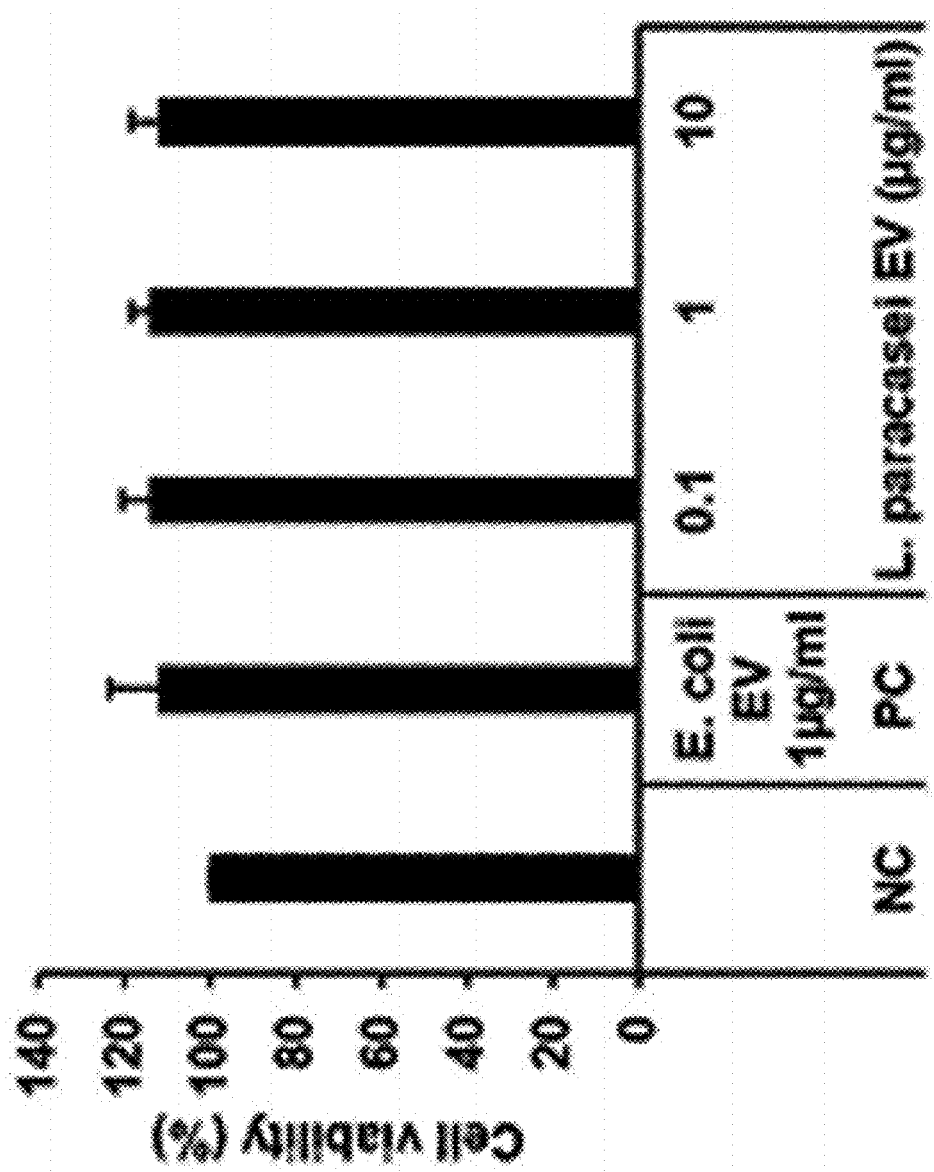
FIGS. 2A and 2B are views illustrating the results of confirming cytotoxicity and inflammation induction effects of the extracellular vesicle derived from *Lactobacillus paracasei* according to an example of the present invention.
Figure 2B:
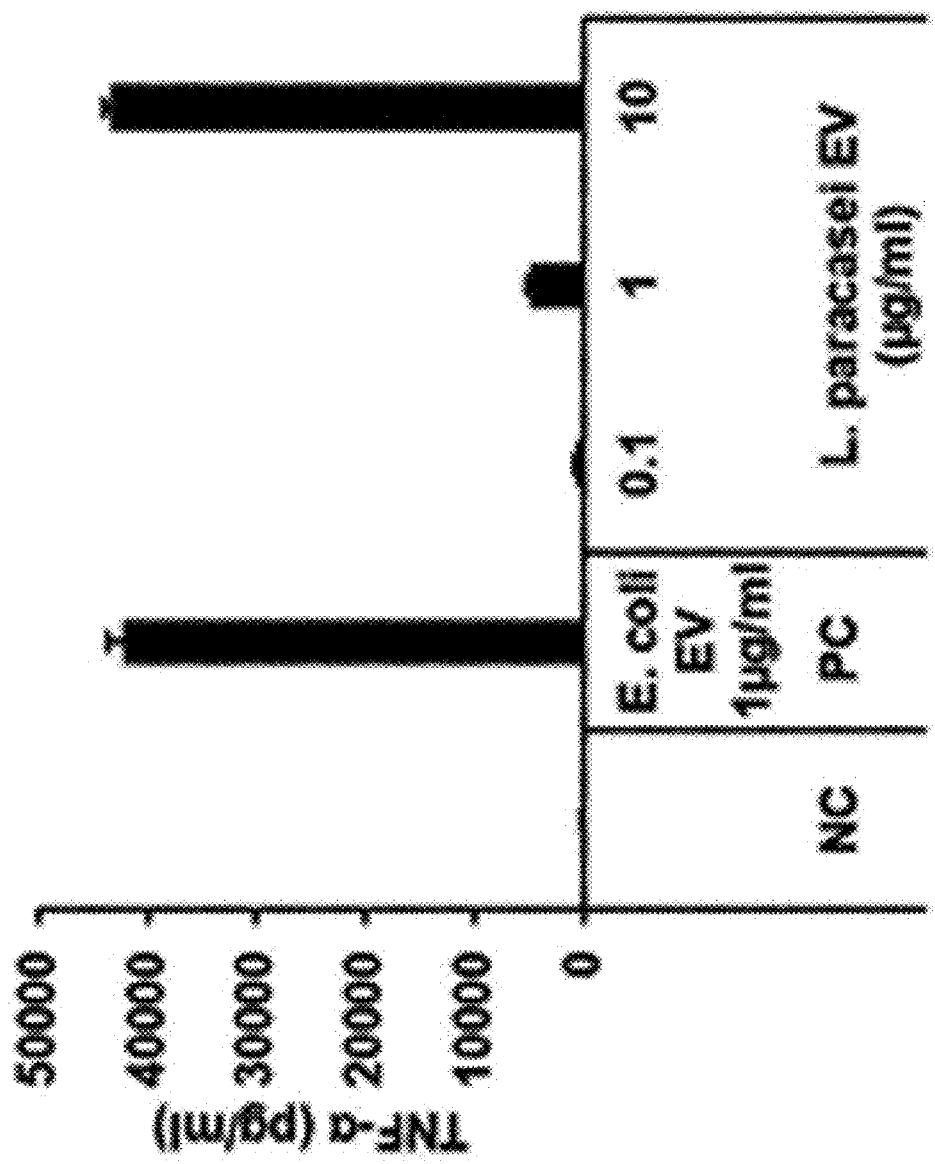

As illustrated in FIG. 2A, it was confirmed that the extracellular vesicle derived from *Lactobacillus paracasei* did not affect the viability of cells, and as illustrated in FIG. 2B, it was confirmed that when treated at a high concentration of 10 μg/mL or more, the extracellular vesicle derived from *Lactobacillus paracasei* promoted the secretion of an inflammatory mediator in a mouse macrophage cell line.

Example 4. Confirmation of Anti-inflammatory Effects of Extracellular Vesicles Derived from *Lactobacillus paracasei*

In order to confirm anti-inflammatory effects of the extracellular vesicle derived from *Lactobacillus paracasei*, the extracellular vesicle derived from *Lactobacillus paracasei* was used to pre-treat a mouse macrophage cell line Raw 264.7 at a concentration of 0.1, 1, 10, and 50 μg/mL, the cells were cultured, and then the secretion amount of TNF-α was measured. More specifically, after Raw 264.7 cells were aliquoted into a 48-well plate at a concentration of 5×10 cells per well, an extracellular vesicle derived from *Lactobacillus paracasei*, which had been diluted with a DMEM serum-free medium, or *Lactobacillus paracasei* prepared in the same manner as in Example 2 was used to treat the aliquoted Raw 264.7 cells, and the cells were cultured for 12 hours. Then, the samples were treated again with the extracellular vesicle derived from *Escherichia coli* at a concentration of 1 μg/mL, followed by culturing for additional 12 hours. Then, the secretion amount of TNF-α was measured in the same manner as in Example 3. The results are illustrated in FIG. 3.

Figure 3:
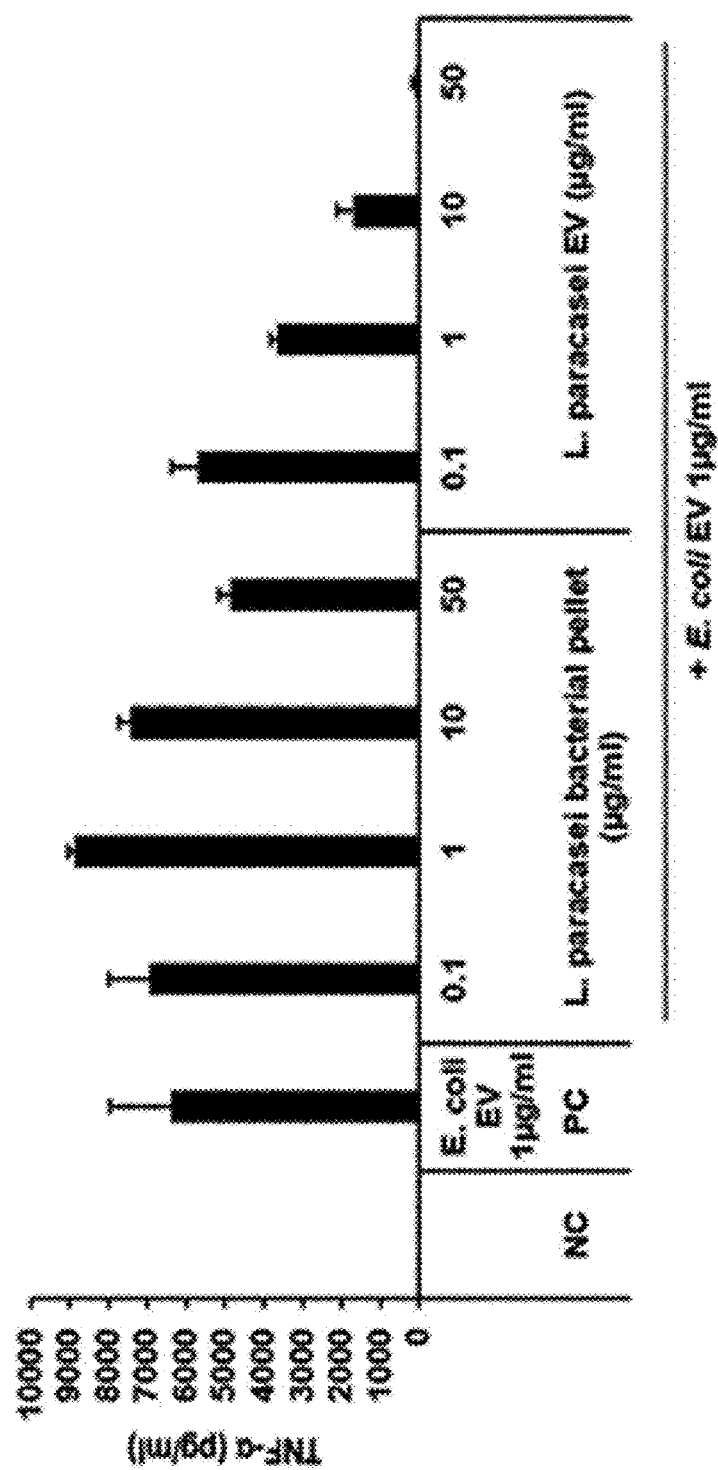
FIG. 3 is a view illustrating the results of confirming anti-inflammatory effects of the extracellular vesicle derived from *Lactobacillus paracasei* according to an example of the present invention.

As illustrated in FIG. 3, it was confirmed that the sample pre-treated with *Lactobacillus paracasei* bacterial cells failed to significantly decrease the secretion of TNF-α by the extracellular vesicle derived from *Escherichia coli*, whereas in the sample treated with the extracellular vesicle derived from *Lactobacillus paracasei*, the secretion of TNF-α by the extracellular vesicle derived from *Escherichia coli* was significantly decreased in a concentration-dependent manner. Through the result, it could be confirmed that an inflammatory response induced by pathogenic bacteria or the extracellular vesicle derived from pathogenic bacteria could be effectively suppressed using the extracellular vesicle derived from *Lactobacillus paracasei*.

Example 5: Confirmation of Effects of Extracellular Vesicle Derived from *Lactobacillus paracasei* on Suppression of LPS-Induced Inflammatory Response 5.1. qRT-PCR Experiment In order to confirm the effects of the extracellular vesicle derived from *Lactobacillus paracasei* on the suppression of a lipopolysaccharide (LPS)-induced inflammatory response, an HT29 cell line as a colorectal cancer cell line was treated with LPS and/or the extracellular vesicle derived from *Lactobacillus paracasei*. More specifically, after an HT29 cell line was cultured in a DMEM medium supplemented with a 10% fetal bovine serum (FBS), 100 U/mL of penicillin, and 100 μg/mL of streptomycin, cells were washed using phosphate buffered saline. Then, after culture in a serum-free DMEM medium for 3 hours, the extracellular vesicle derived from *Lactobacillus paracasei* was used for pre-treatment at a concentration of 500 ng/mL, and the cells were cultured for 12 hours. The cultured cells were treated with 1 μg/mL of LPS, and then cultured again for 12 hours. Then, a quantitative reverse transcriptase polymerase chain reaction (qRT-PCR) was performed. In order to perform the qRT-PCR, after the total RNA was primarily extracted from the cultured cells according to the protocol provided by the manufacturer using a TRIZOL reagent (Invitrogen), the amount of RNA was measured using a NanoDrop 2000 Spectrophotometer, and then cDNA was synthesized using an M-MLV reverse transcription enzyme, and qRT-PCR was performed using the synthesized cDNA as a template. The qRT-PCR was performed using Quant3 Studio Real-time PCR Systems (Applied Biosystems), and for quantification, the qRT-PCR was performed according to the protocol provided by the manufacturer using a CyberGreen qPCR Mastermix kit. The used primer sequences are described in Table 1, and the results are illustrated in FIGS. 4A and 4B.

TABLE 1

| Gene | Primers (5' to 3') | SEQ ID No. |
|---|---|---|
| IL1α | TCAAGGAGAGCATGGTGGTA | 1 |
| | GTGCTGACCTAGGCTTGATG | 2 |
| IL1β | AGCTCGCCAGTGAAATGATG | 3 |
| | CGGAGATTCGTAGCTGGATG | 4 |
| IL2 | AACCTCTGGAGGAAGTGCTA | 5 |
| | AATGGTTGCTGTCTCATCAGC | 6 |
| IL3 | CACGCGACATCCAATCCATA | 7 |
| | TCAAAGTCGTCTGTTGAGCC | 8 |
| IL4 | CCGAGTTGACCGTAACAGAC | 9 |
| | GTTCTCTCTGGGCTTTGTAGG | 10 |
| TNFα | ATCATCTTCTCGAACCCCGA | 11 |
| | GTTATCTCTCAGCTCCACGC | 12 |
| IL10 | CCTGCCTAACATGCTTCGAG | 13 |
| | GTCTTGGTTCTCAGCTTGGG | 14 |
| TGFβ | GACTCGCCAGAGTGGTTATC | 15 |
| | GGTAGTGAACCCGTTGATGT | 16 |
| β-actin | AACTACCTTCAACTCCATC | 17 |
| | CTTGCTGATCCACATCTG | 18 |

Figure 4A:
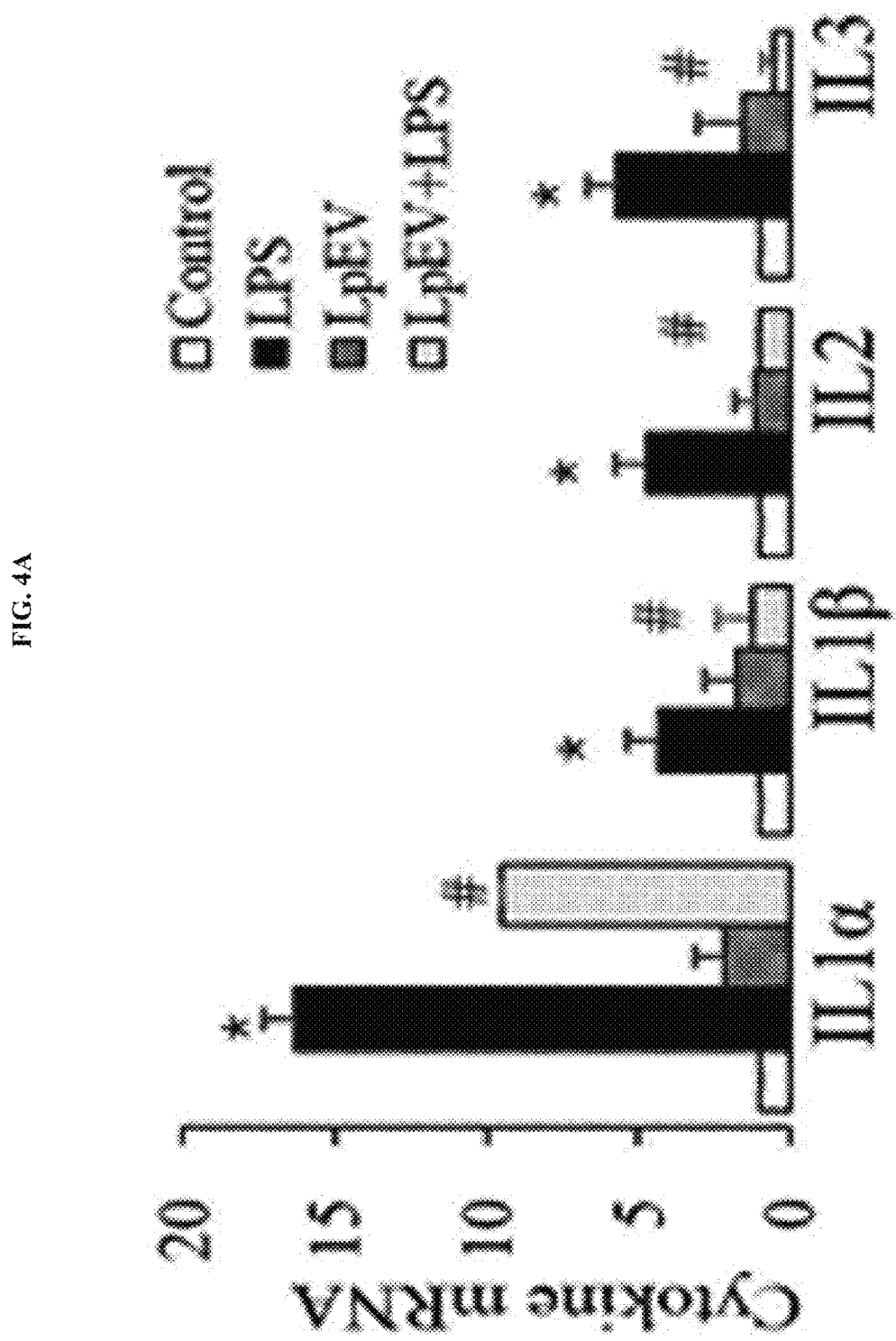
FIGS. 4A and 4B are views illustrating the results of confirming the effects of the extracellular vesicle derived from *Lactobacillus paracasei* according to an example of the present invention on the suppression of LPS-induced inflammatory responses by qRT-PCR.
Figure 4B:
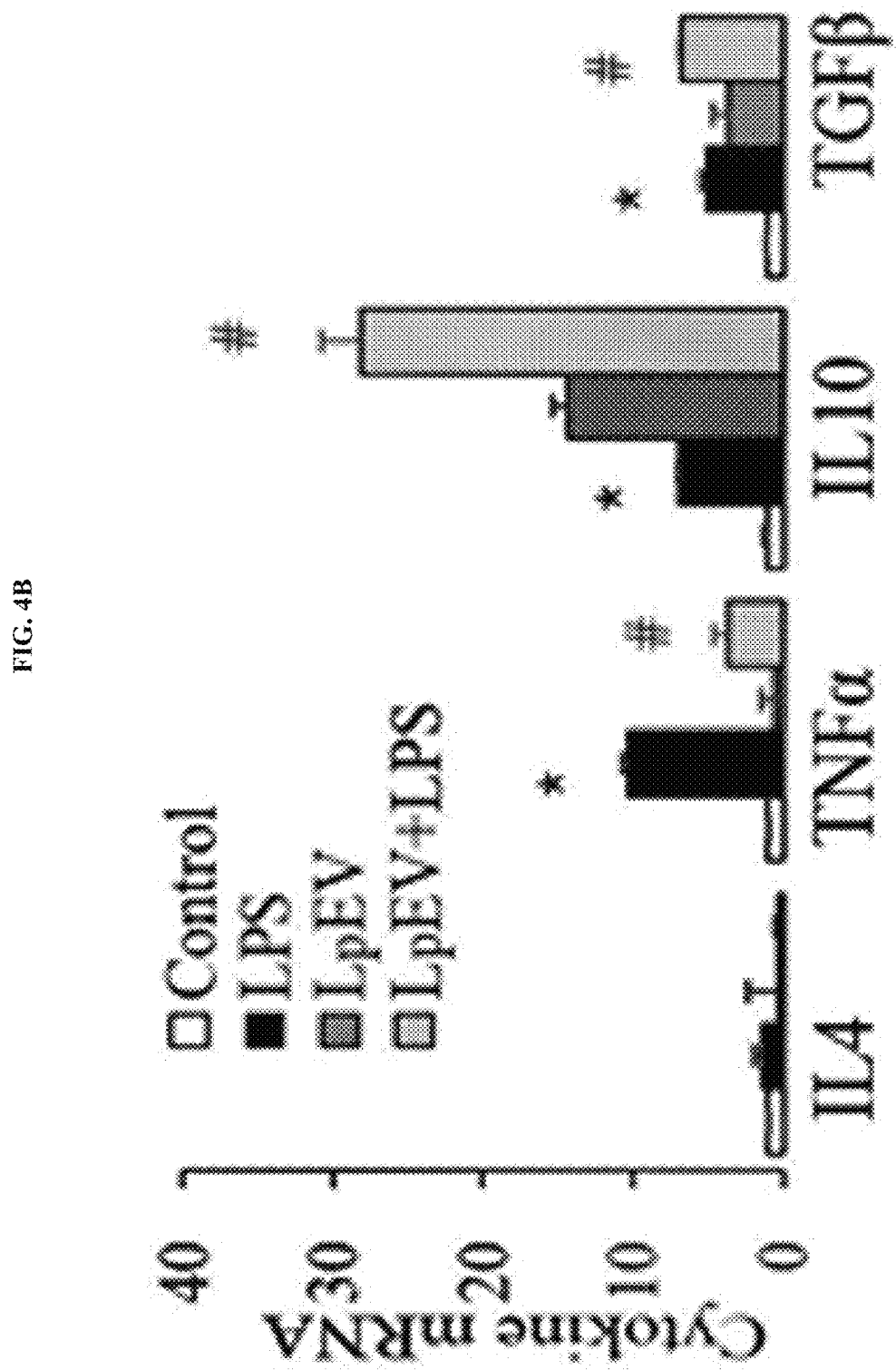

As illustrated in FIGS. 4A and 4B, it was confirmed that since the inflammatory response was promoted by LPS, the expression levels of pro-inflammatory cytokines IL-1α, IL-1β, IL-2, IL-3, and TNF-α were increased, but in cells (LpEV) pre-treated with the extracellular vesicle derived from *Lactobacillus paracasei*, the expression of the pro-inflammatory cytokines, which had been increased, was suppressed. Further, it was confirmed that the expression of IL-10 and TGF-β was increased.

5.2. Western Blotting Experiment

In order to confirm effects of the extracellular vesicle derived from *Lactobacillus paracasei* on the suppression of a lipopolysaccharide (LPS)-induced inflammatory response, western blotting was performed. After the cells prepared in the same manner as in Example 5.1 were washed twice using a cold phosphate buffered saline and lysed using a RIPA lysis buffer (50 mM Tris-HCl (pH 7.4), 150 mM NaCl, 1.0% NP-40, 0.5% sodium deoxycholate, 0.1% sodium dodecyl sulfate (SDS), 50 mM NaF, 0.1 mM phenylmethanesulfonylfluoride, and 0.5% protease inhibitor cocktail), cell debris were thoroughly removed by centrifugation at 4° C. and 12,000×g for 5 minutes, and then the amount of protein was measured using a Pierce BCA Protein Assay kit (Thermo Fisher Scientific). Then, protein separation was performed by subjecting 40 μg of protein to SDS-PAGE (Bio-Rad Laboratories) using a 8 to 12% SDS-polyacrylamide gel, the protein which had been separated was transferred to a Hybond™-ECL nitrocellulose membrane (Amersham Bioscience). Then, the membrane to which the protein had been transferred was blocked at room temperature for 1 hour using TBST supplemented with 5% skim milk, and then treated with primary antibodies diluted at 1:2,000, and allowed to react at 4° C. for 16 hours. Then, the membrane was washed three times using TBST, and then treated with secondary antibodies to which HRP diluted at 1:2,000 had been bound, allowed to react at room temperature for 1 hour, and observed using an ECL detection system (Amersham). Antibodies against COX-2 and activated MMP9 were purchased from SantaCruz, antibodies against NFκ and iNOS were purchased from BioLegend, and antibodies against β-actin, phospho-Iκκ, and Iκ were purchased from Cell Signaling Technology and used. The results are illustrated in FIGS. 5A and 5B.

Figure 5A:
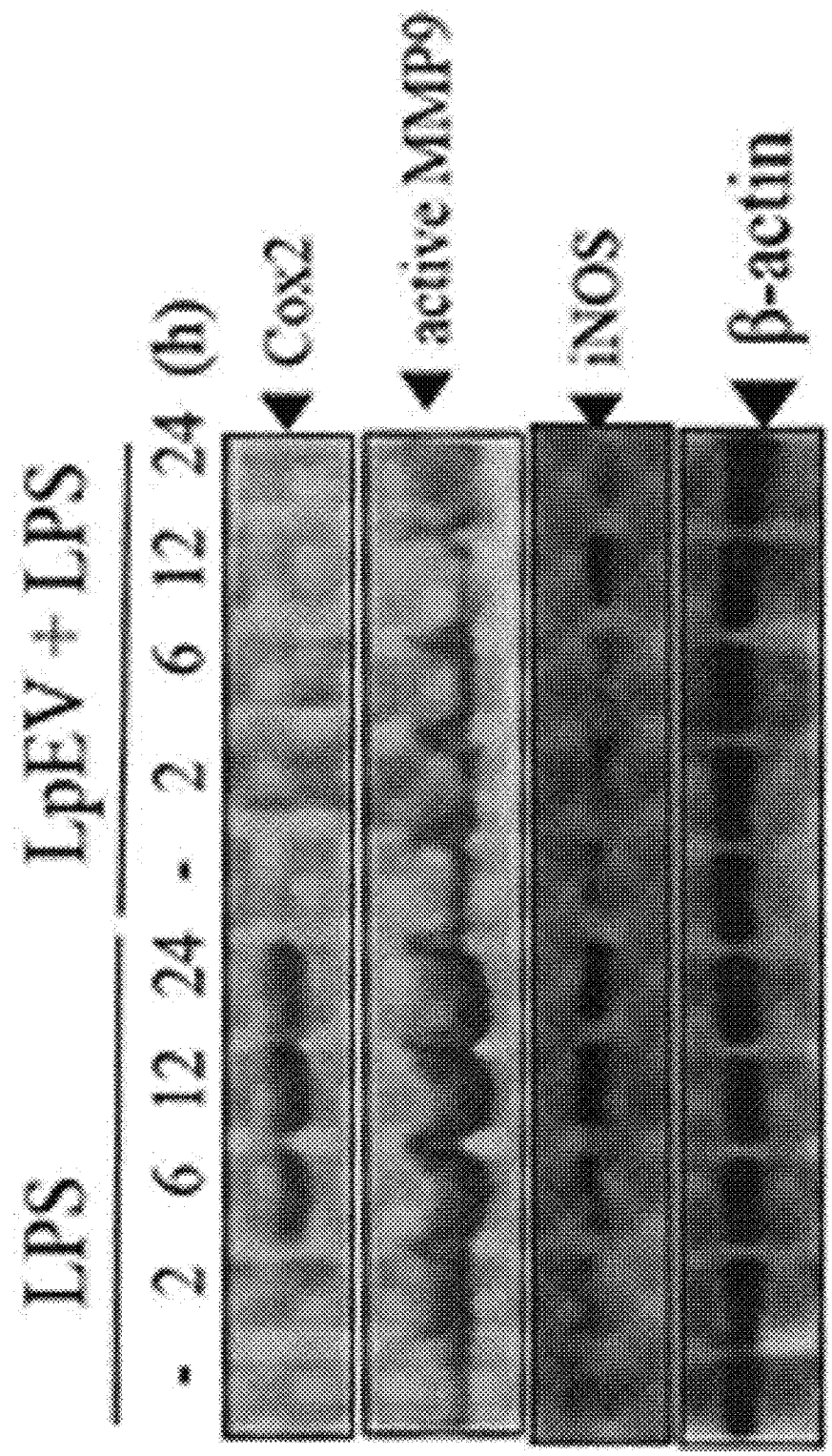
FIGS. 5A and 5B are views illustrating the results of confirming the effects of the extracellular vesicle derived from *Lactobacillus paracasei* according to an example of the present invention on the suppression of LPS-induced inflammatory responses by western blotting.
Figure 5B:
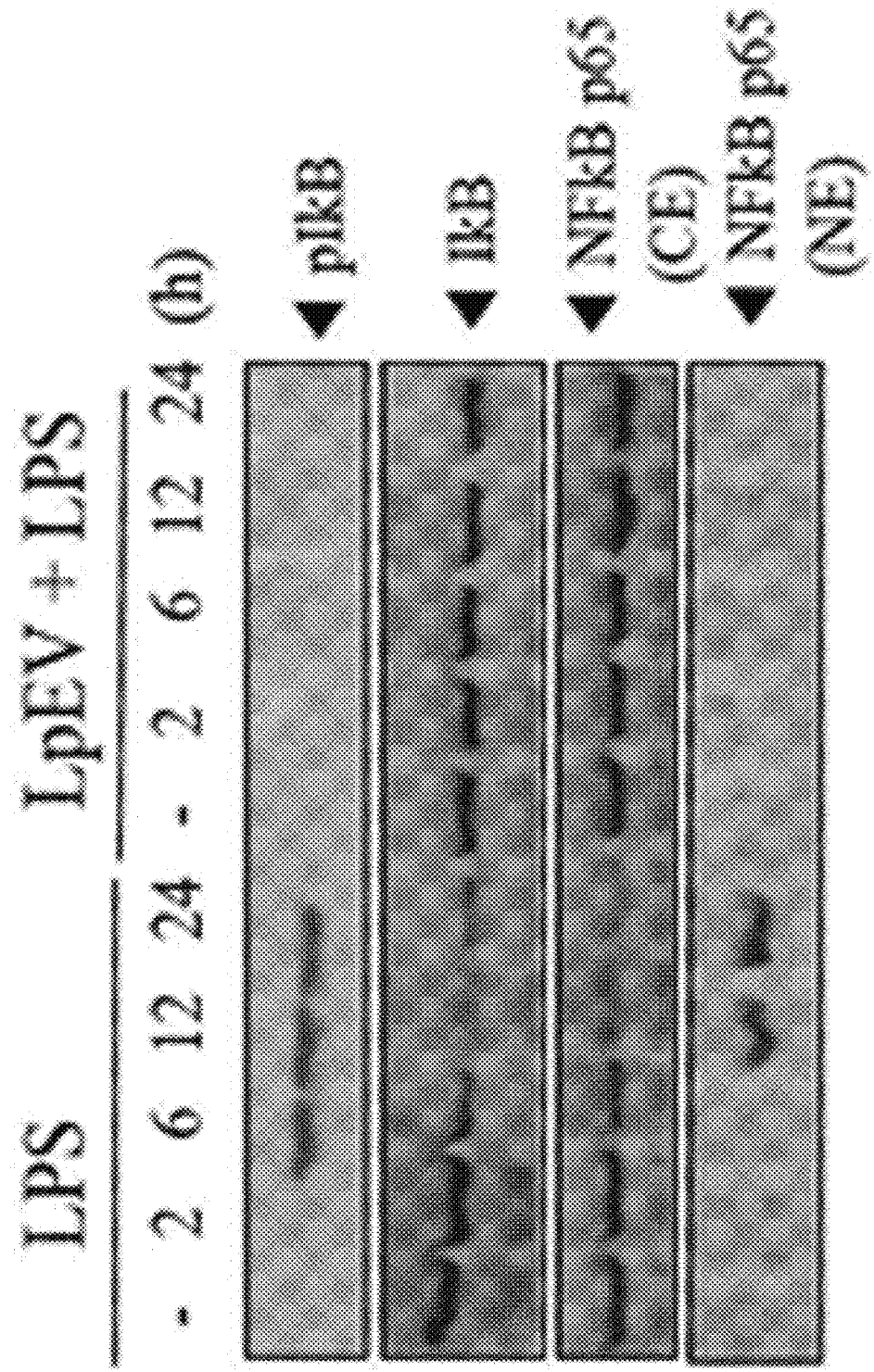

As illustrated in FIGS. 5A and 5B, it was confirmed that in the control treated with the LPS alone, the expression levels of Cox2, activated MMP9, and iNOS were increased according to the LPS treatment time (2, 6, 12, and 24 hours) and the phosphorylation of Iκ was promoted, and it was confirmed that the transfer of NFκ into the nucleus was promoted. However, it was confirmed that in the case of cells pre-treated with the extracellular vesicle derived from *Lactobacillus paracasei*, the expression of the inflammatory proteins induced by the LPS treatment was decreased, the phosphorylation of Iκ was suppressed, and the transfer of NFκ into the nucleus was suppressed. Through the results, it could be confirmed that *Lactobacillus paracasei* could effectively suppress the inflammatory response induced by LPS.

Example 6: Confirmation of Effects of Extracellular Vesicle Derived from *Lactobacillus paracasei* on Suppression of Inflammatory Response in DSS-Induced Colitis 6.1. Histological Analysis In order to confirm effects of the extracellular vesicle derived from *Lactobacillus paracasei* on the treatment of DSS-induced colitis, colitis was induced by treating mice with dextran sodium sulfate (DSS). More specifically, after 7-week-old male C57BL/6 mice were bred under general conditions for a week as an acclimation period, 2 w/v % DSS (MP Biomedicals, LLC) was mixed with drinking water and provided for 5 days. A control was fed with general drinking water for 5 days. 10 mg per mouse of the extracellular vesicle derived from *Lactobacillus paracasei* was injected into mice using an oral gavage on day 1 of DSS administration. Then, 13 days after the initiation of the experiment, the mice were anesthetized, the colons were extracted, and then the length from the ileocecal junction to the rectum was measured, and the extracted colon was stored at −80° C. for a subsequent experiment. The disease activity index (DAI), the body weight, the stool consistency, and the bloody stool level were recorded daily. More specifically, the disease activity index was indicated as 1, 2, 3, and 4 when the body weight was 100% or more, 90 to 100%, 80 to 90%, and 80% or less with respect to the body weight on day 0, respectively, and the stool consistency was indicated as 1, 2, 3, and 4 when the stool was normal, slightly thinner, thinner, and watery, respectively. In addition, the bloody stool level was indicated as 1, 2, 3, and 4 when the stool was normal, when blood was in the stool, when blood was observed in the anus, and when blood was observed in both the stool and the anus, respectively. The results are illustrated in FIGS. 6A to 6E.

Figure 6A:
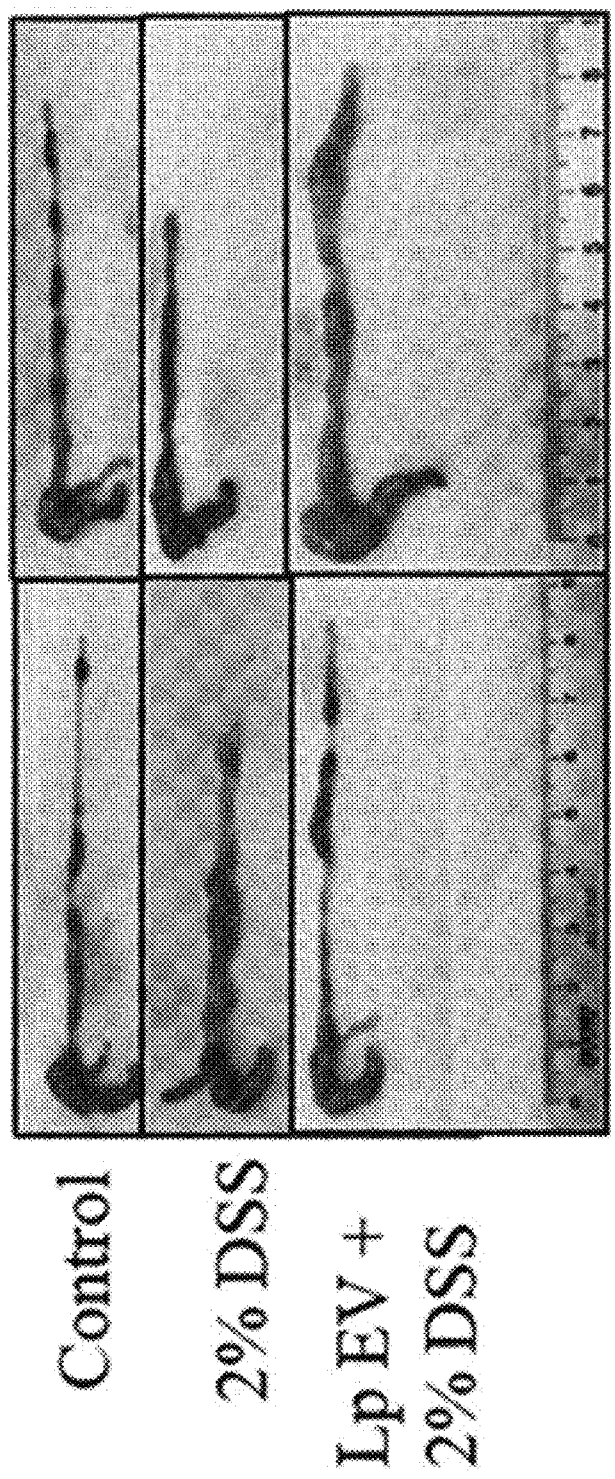
FIGS. 6A to 6E are views illustrating the results of confirming the effects of the extracellular vesicle derived from *Lactobacillus paracasei* on the suppression of inflammatory responses in DSS-induced colitis according to an embodiment of the present invention by a histological analysis method.
Figure 6B:
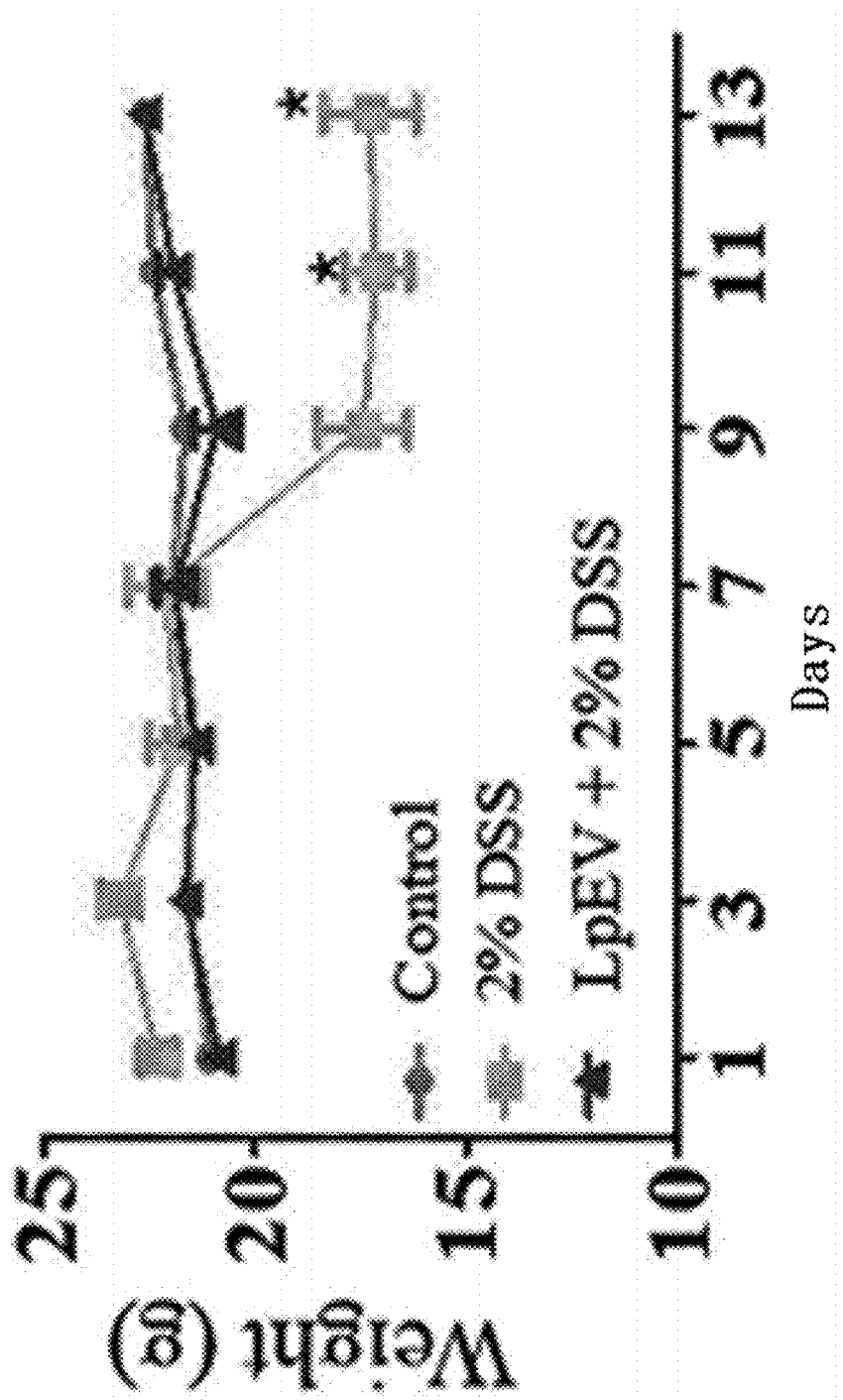
Figure 6C:
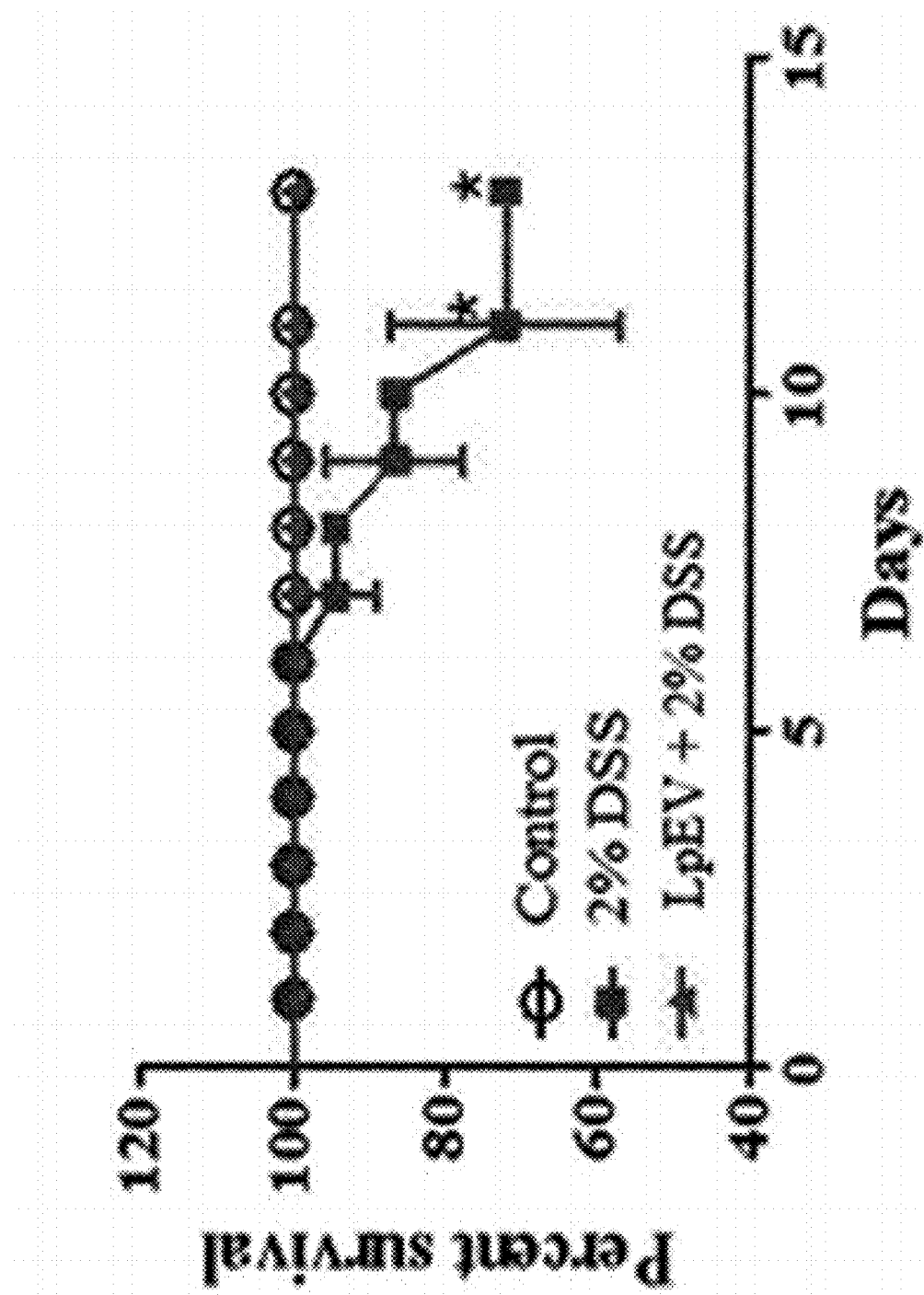
Figure 6D:
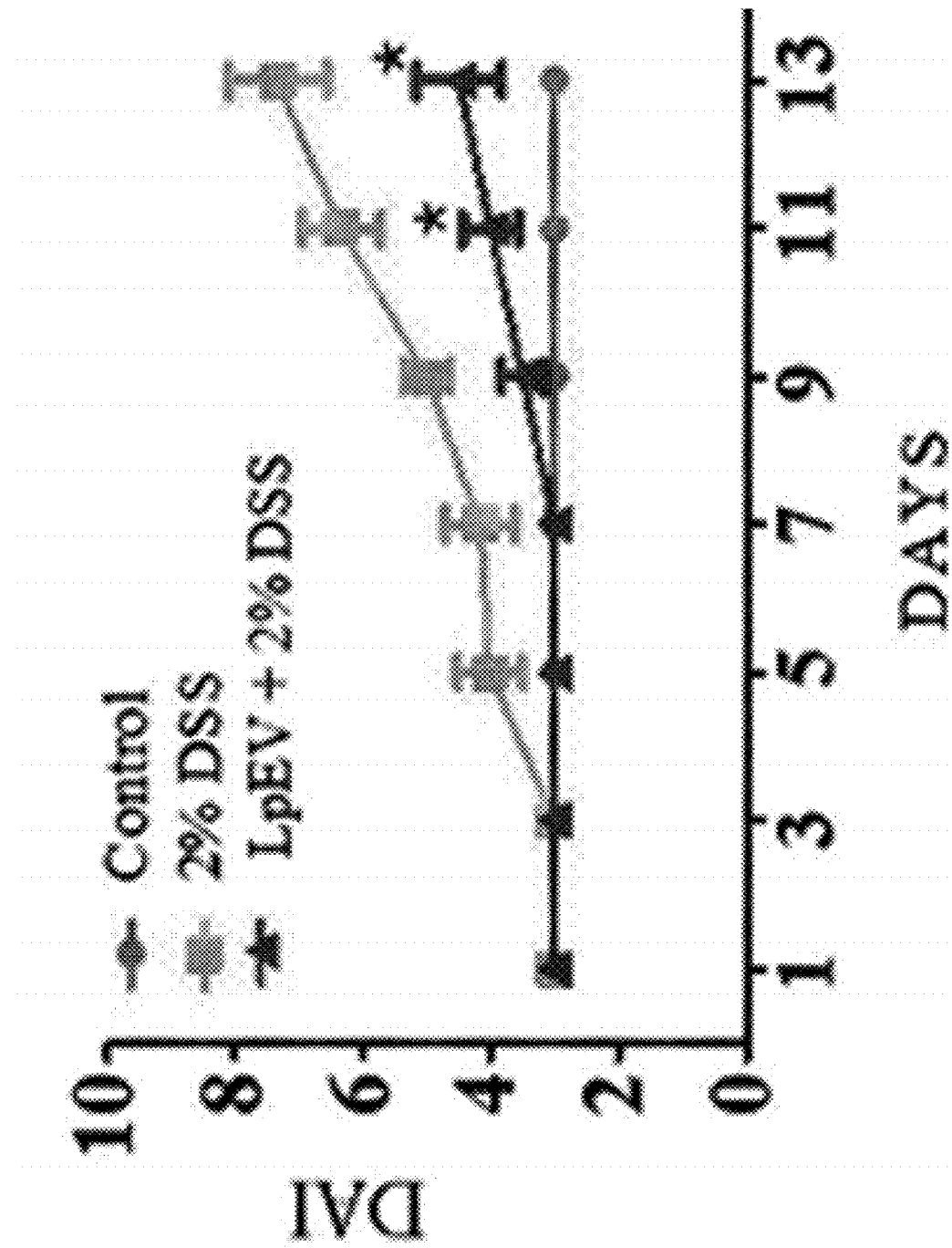
Figure 6E:
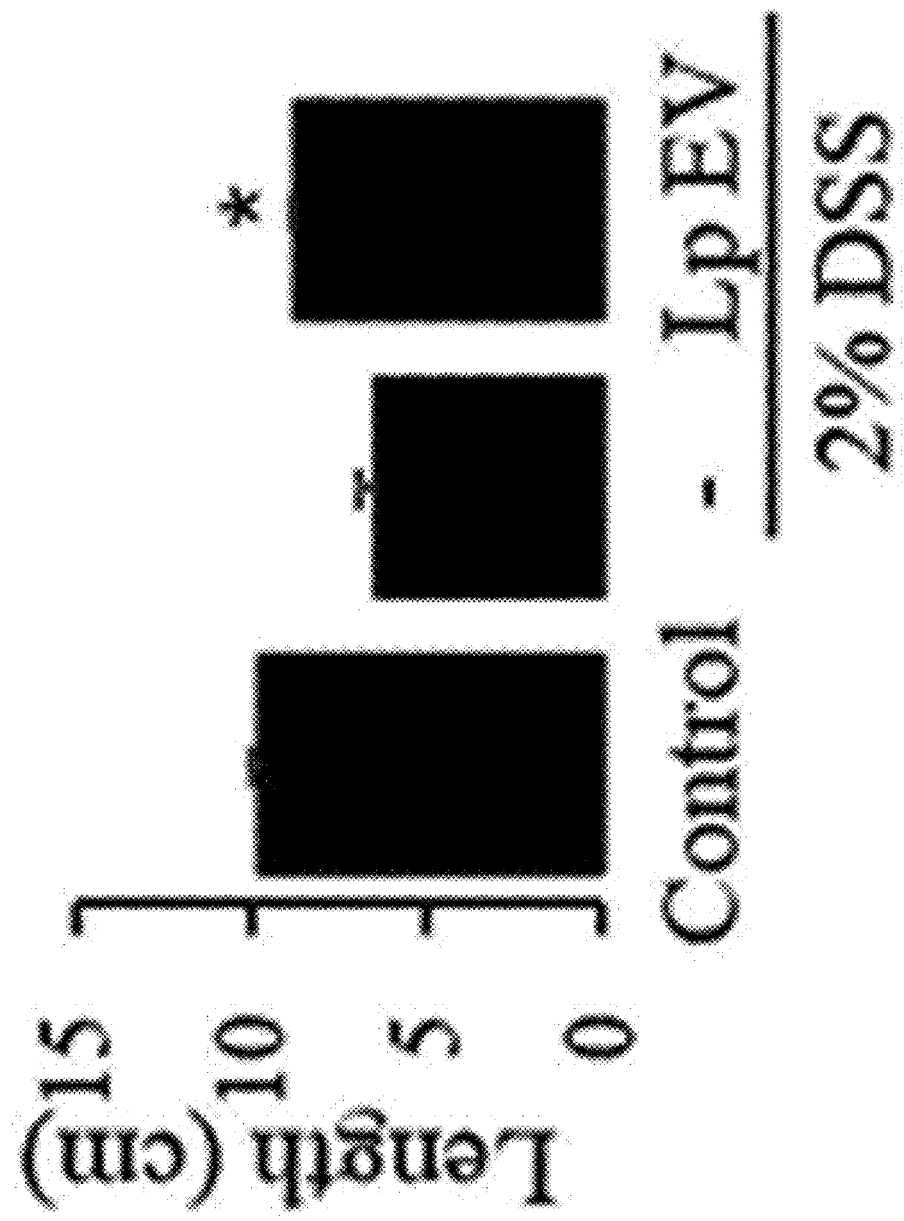
Figure 7A:
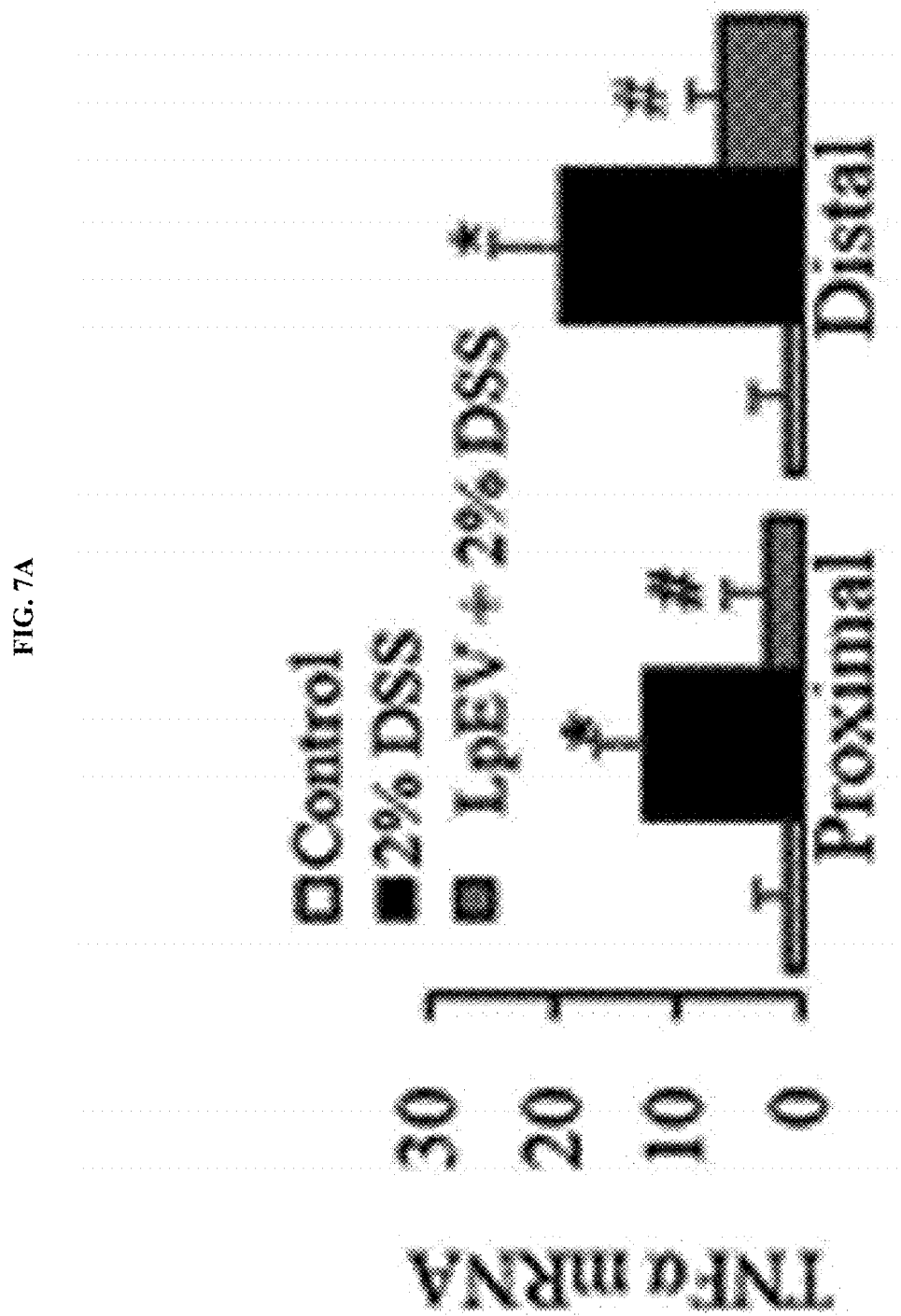
FIGS. 7A to 7D are views illustrating the results of confirming the effects of the extracellular vesicle derived from *Lactobacillus paracasei* on the suppression of inflammatory responses in DSS-induced colitis according to an embodiment of the present invention by qRT-PCR.
Figure 7B:
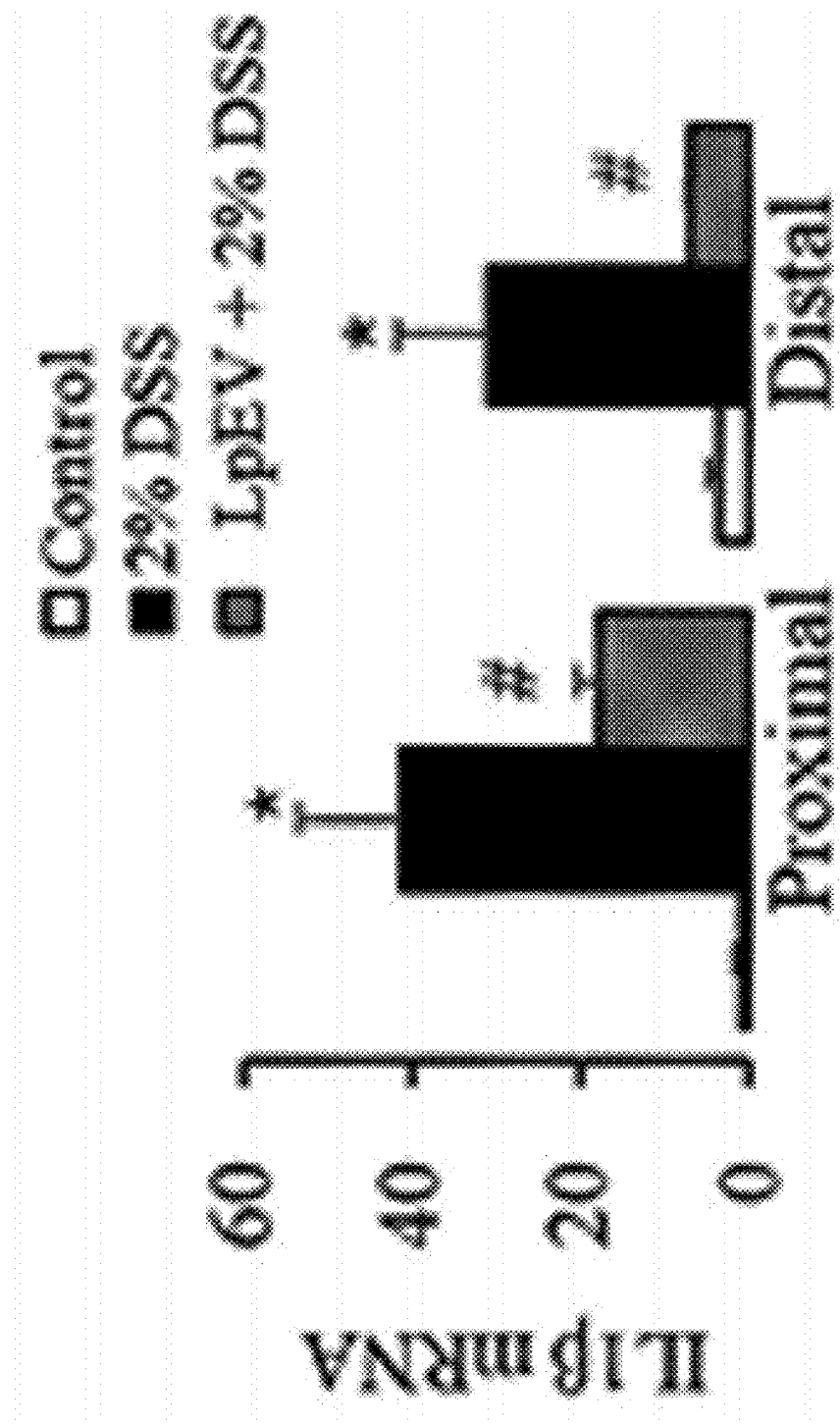
Figure 7C:
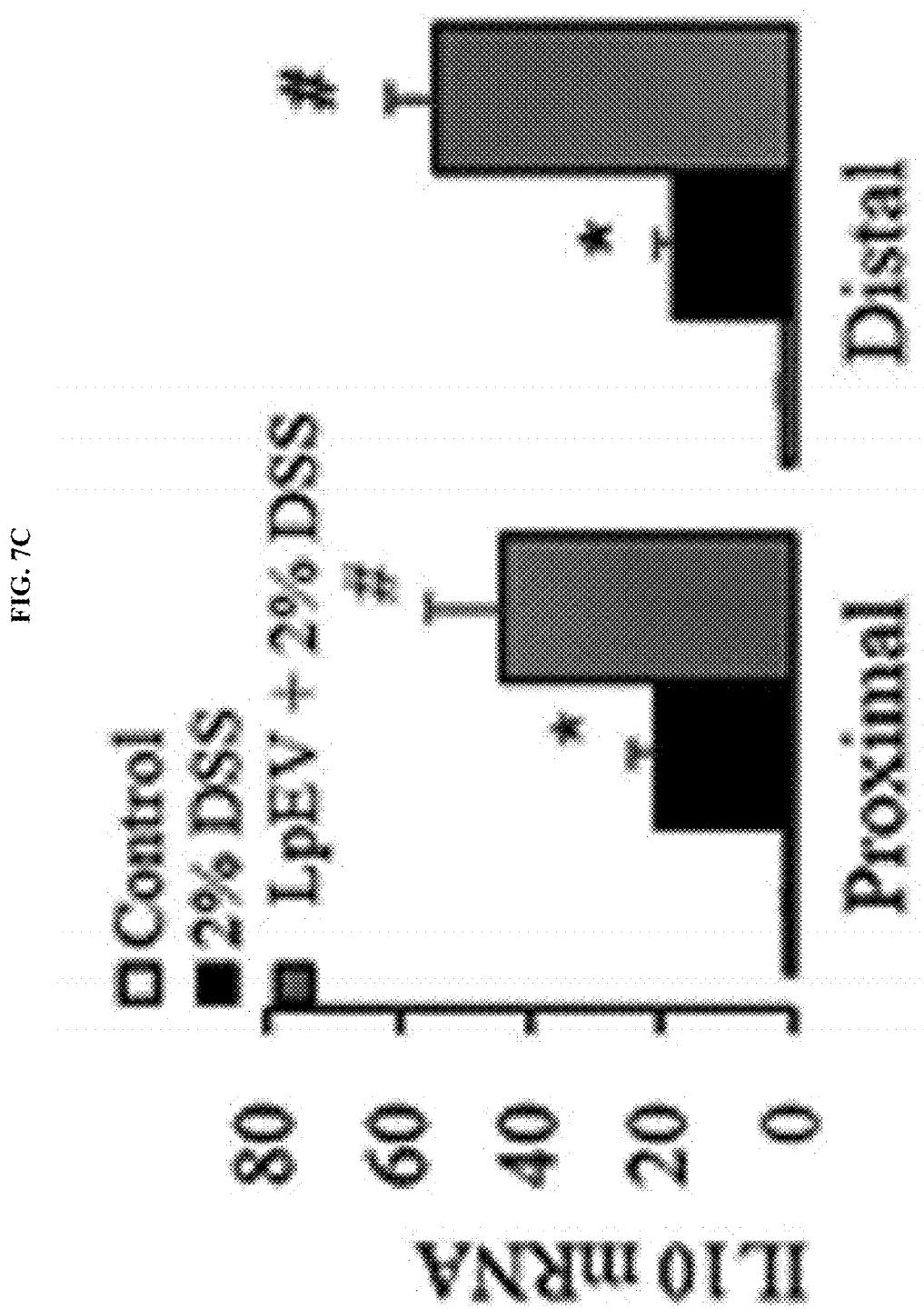
Figure 7D:
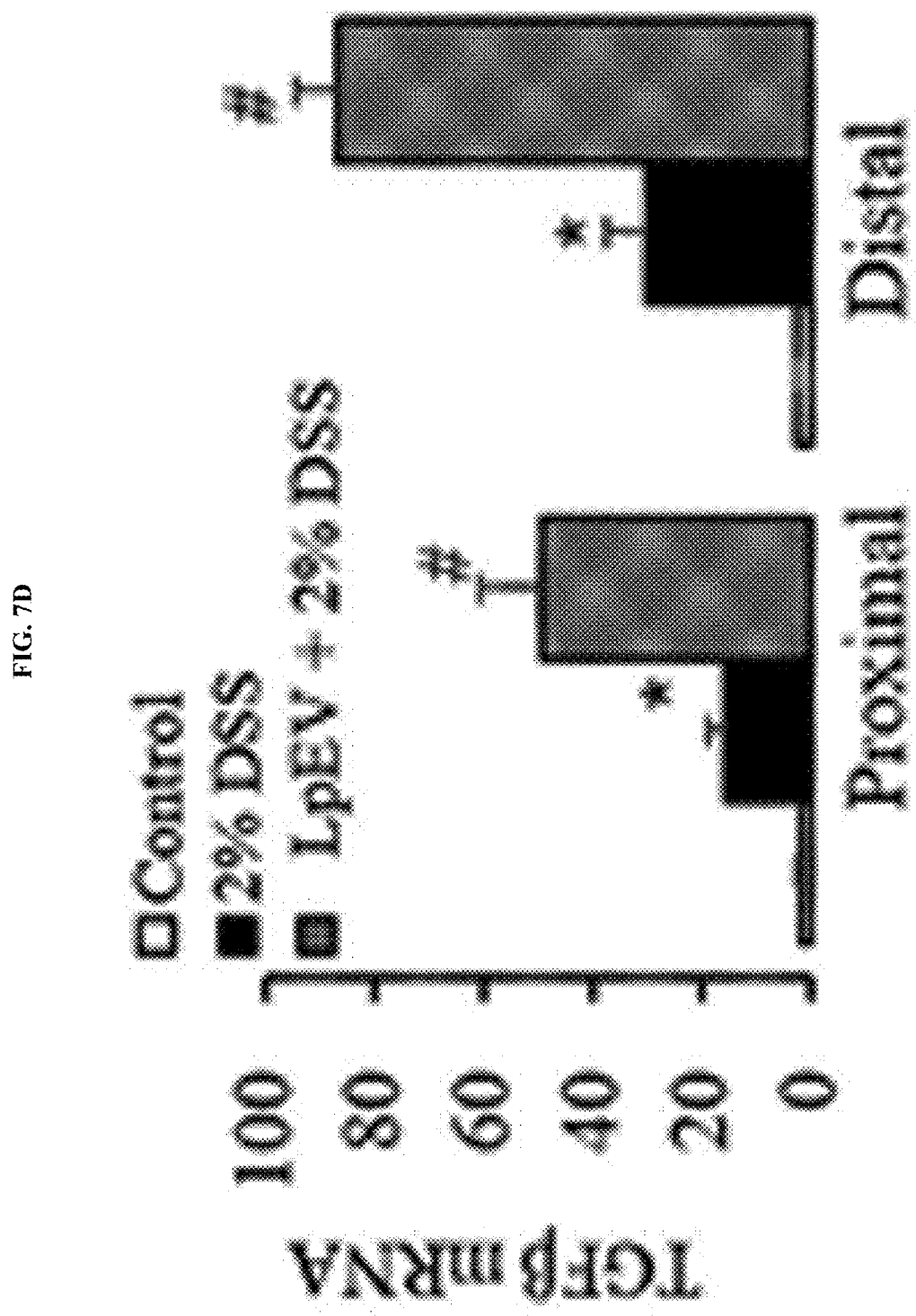

It was confirmed that the length of the colon was shortened in the mice to which the DSS was administered, but the initial length of the colon was maintained in the experimental group to which the extracellular vesicle derived from *Lactobacillus paracasei* was administered together with the DSS (FIGS. 6A and 6E). Further, it was confirmed that in the experimental group to which the extracellular vesicle derived from *Lactobacillus paracasei* was administered together with the DSS, the body weight was maintained at a level similar to that of the control, and the disease activity index was also decreased as compared to that of the mice to which the DSS was administered (FIGS. 6B and 6D). In addition, it was confirmed that the experimental group to which the extracellular vesicle derived from *Lactobacillus paracasei* had been administered together exhibited the same viability as that of the control (FIG. 6C). Through the results, it could be confirmed that the extracellular vesicle derived from *Lactobacillus paracasei* could effectively suppress the colitis induced by DSS.

6.2. qRT-PCR Experiment

In order to confirm effects of the extracellular vesicle derived from *Lactobacillus paracasei* on the treatment of DSS-induced colitis, qRT-PCR was performed in the same manner as in Example 5.1 by extracting mRNA from the colon stored at −80° C. The results are illustrated in FIGS. 7A to 7D.

As illustrated in FIGS. 7A to 7D, it was confirmed that in the mice (LpEV) pre-treated with the extracellular vesicle derived from *Lactobacillus paracasei*, the expression of TNF-α and IL-1β as a pro-inflammatory cytokine, which had been increased, was remarkably decreased, and the expression of IL-10 and TGF-β was increased. Through the result, it could be confirmed that the inflammatory response induced by DSS was effectively suppressed by the extracellular vesicle derived from *Lactobacillus paracasei*.

6.3. Western Blotting Experiment

In order to confirm effects of the extracellular vesicle derived from *Lactobacillus paracasei* on the treatment of DSS-induced colitis, western blotting was performed in the same manner as in Example 5.2 by extracting protein from the colon stored at −80° C. The results are illustrated in FIGS. 8A and 8B.

Figure 8A:
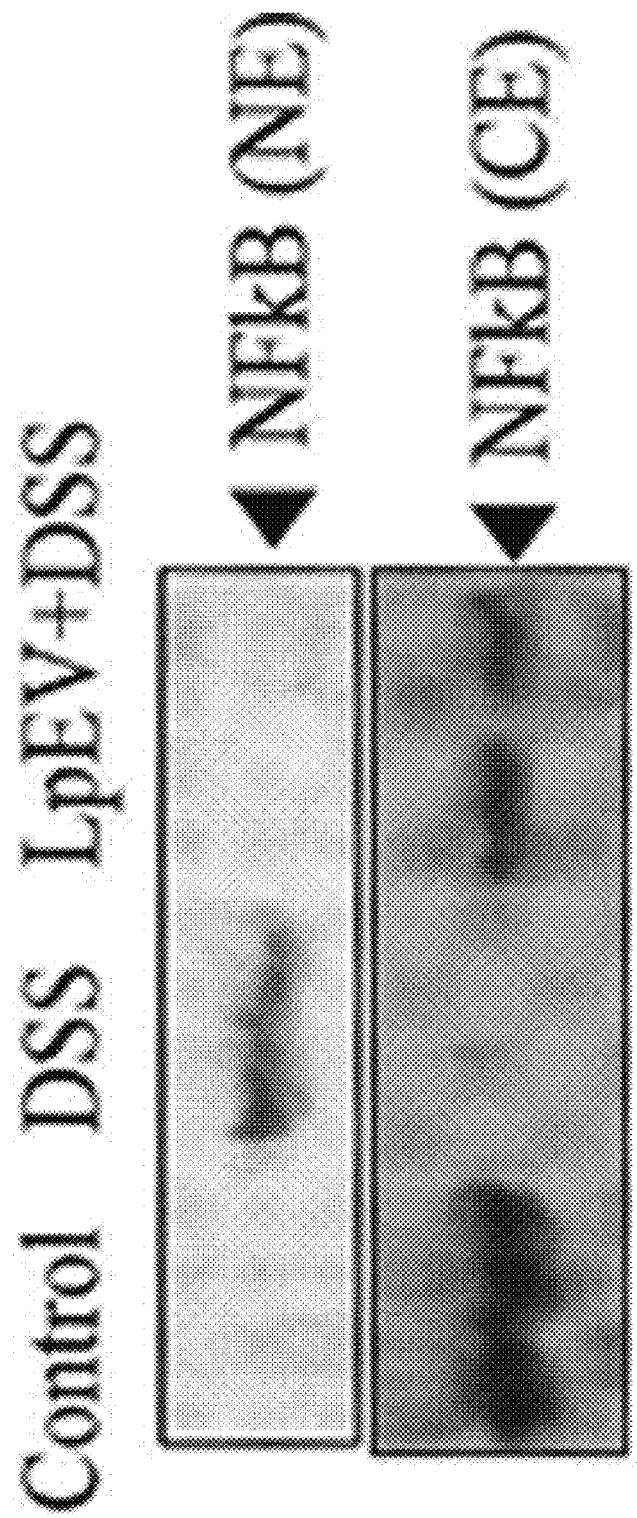
FIGS. 8A and 8B are views illustrating the results of confirming the effects of the extracellular vesicle derived from *Lactobacillus paracasei* on the suppression of inflammatory responses in DSS-induced colitis according to an embodiment of the present invention by western blotting.
Figure 8B:
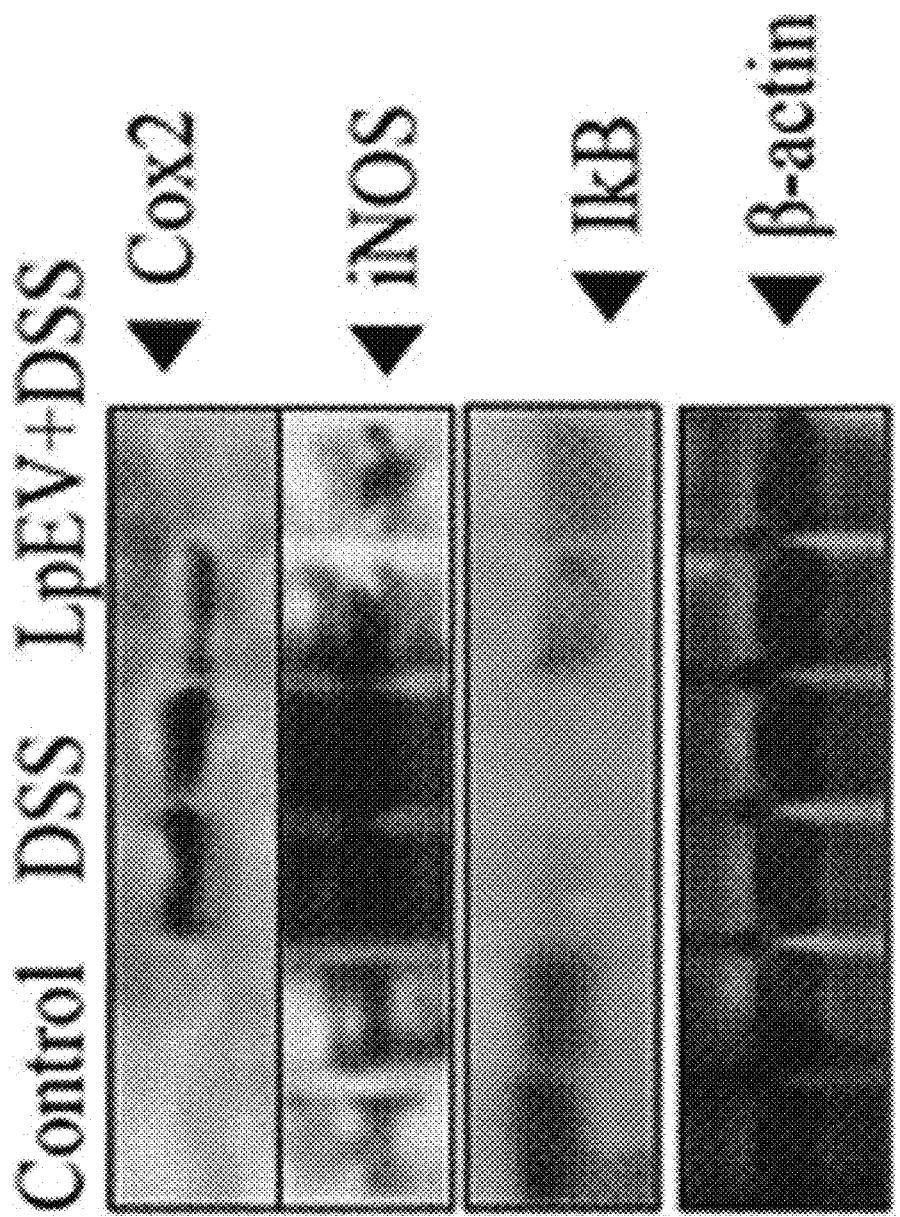

As illustrated in FIGS. 8A and 8B, it was confirmed that in the mice treated with the extracellular vesicle derived from *Lactobacillus paracasei*, the expression level of the inflammatory protein induced by the treatment with DSS was decreased, the degradation of Iκ was suppressed due to the suppression of phosphorylation of Iκ, and the transfer of NFκ into the nucleus was suppressed. Through the result, it could be confirmed that the inflammatory response induced by DSS was effectively suppressed by the extracellular vesicle derived from *Lactobacillus paracasei*.

Example 7. Confirmation of Anti-Cancer Effects of Extracellular Vesicles Derived from *Lactobacillus paracasei*

In order to confirm anticancer effects of the extracellular vesicle derived from *Lactobacillus paracasei*, cancer was induced by injecting CT26 cells, as mouse colorectal cancer cells, into mice. More specifically, after 6-week-old male C57BL/6 mice were bred under general conditions for 3 days as an acclimation period, 20 μg of the extracellular vesicle derived from *Lactobacillus paracasei* was orally administered for 5 days. PBS was orally administered to a control (PBS) for 5 days. On day 8 after the initiation of the experiment, $1\times10^6$ CT26 cells as mouse colorectal cancer cells were subcutaneously injected into the mice. Then, 20 μg of the extracellular vesicle derived from *Lactobacillus paracasei* or PBS was orally administered once daily, for 5 days per week, for 3 weeks while measuring the size of cancer.

Figure 9:
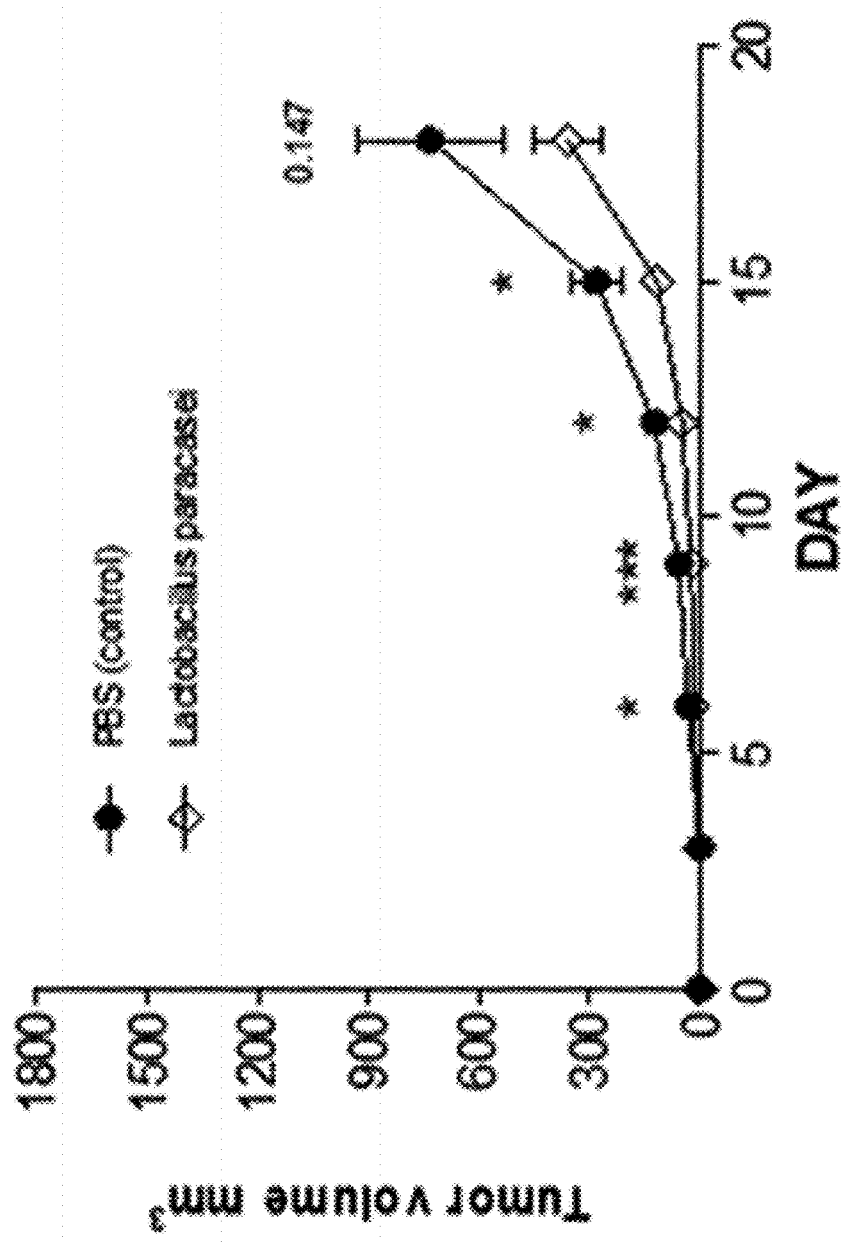
FIG. 9 is a view illustrating the results of measuring the size of cancer over time after the extracellular vesicle derived from *Lactobacillus paracasei* is orally administered in a cancer model prepared by transplanting cancer cells according to an example of the present invention.

As illustrated in FIG. 9, it was confirmed that in the control to which PBS had been administered alone, the size of cancer was exponentially increased, but in the experimental group to which the extracellular vesicle derived from *Lactobacillus paracasei* had been orally administered, the size of cancer was smaller than that of the control by about 50%. Through the results, it could be confirmed that the extracellular vesicle derived from *Lactobacillus paracasei* could effectively suppress the growth of cancer.

Through the results, it was confirmed that the extracellular vesicle derived from *Lactobacillus paracasei* of the present invention exhibited anti-inflammatory effects by effectively suppressing the expression of TNF-α and the like known as factors of various chronic inflammation diseases, and exhibited effects of preventing and/or treating various inflammation diseases and cancers by efficiently suppressing the growth of cancer in a cancer animal model, so that it is expected that the extracellular vesicle derived from *Lactobacillus paracasei* of the present invention can be used for alleviating, preventing, or treating various inflammation diseases and cancers.

The above-described description of the present invention is provided for illustrative purposes, and those of ordinary skill in the art to which the present invention pertains will understand that the present invention can be easily modified into other specific forms without changing the technical spirit or essential features of the present invention. Therefore, it should be understood that the above-described Examples are illustrative only in all aspects and are not restrictive.

INDUSTRIAL APPLICABILITY

Since the extracellular vesicle derived from *Lactobacillus paracasei* according to the present invention may effectively suppress the expression of pro-inflammatory cytokines TNF-α, IL-1β, and the like which are known as factors of various chronic inflammatory diseases, it is expected that the extracellular vesicle derived from *Lactobacillus paracasei* according to the present invention can be broadly used as an agent for alleviating, preventing, or treating various chronic inflammation diseases and cancers having low side effects, so that there is an industrial applicability.

The invention claimed is:

1. A method of alleviating or treating an inflammation disease or a cancer, the method comprising administering to a subject in need thereof a composition comprising an effective amount of an extracellular vesicle derived from *Lactobacillus paracasei*, wherein the extracellular vesicles are isolated from a culturing solution comprising *Lactobacillus paracasei* bacterial cells.

2. The method of claim 1, wherein the composition is a pharmaceutical composition, a food composition, or a cosmetic composition.

3. The method of claim 1, wherein the inflammation disease is any one selected from the group consisting of an inflammatory enteritis, gastritis, asthma, chronic obstructive pulmonary disease (COPD), rhinitis, atopic dermatitis, alopecia, psoriasis, degenerative arthritis, and rheumatoid arthritis.

4. The method of claim 1, wherein the cancer is any one selected from the group consisting of a colorectal cancer, gastric cancer, lung cancer, liver cancer, bile duct cancer, pancreatic cancer, breast cancer, ovarian cancer, renal cancer, bladder cancer, and prostate cancer.

5. The method of claim 1, wherein the inflammation disease is a disease mediated by TNF-α or IL-1β.

6. The method of claim 1, wherein the extracellular vesicle has an average diameter of 10 to 300 nm.

7. The method of claim 1, wherein the extracellular vesicle is secreted naturally or artificially from *Lactobacillus paracasei*.

8. The method of claim 1, wherein the composition is an inhalant composition.

* * * * *

SEQUENCE LISTING

<160> NUMBER OF SEQ ID NOS: 18

<210> SEQ ID NO 1
<211> LENGTH: 20
<212> TYPE: DNA
<213> ORGANISM: Artificial Sequence
<220> FEATURE:
<223> OTHER INFORMATION: IL1 alpha forward primer

<400> SEQUENCE: 1
tcaaggagag catggtggta                                         20

<210> SEQ ID NO 2
<211> LENGTH: 20
<212> TYPE: DNA
<213> ORGANISM: Artificial Sequence
<220> FEATURE:
<223> OTHER INFORMATION: IL1 alpha reverse primer

<400> SEQUENCE: 2
gtgctgacct aggcttgatg                                         20

<210> SEQ ID NO 3
<211> LENGTH: 20
<212> TYPE: DNA
<213> ORGANISM: Artificial Sequence
<220> FEATURE:
<223> OTHER INFORMATION: IL1 beta forward primer

<400> SEQUENCE: 3
agctcgccag tgaaatgatg                                         20

<210> SEQ ID NO 4
<211> LENGTH: 20
<212> TYPE: DNA
<213> ORGANISM: Artificial Sequence
<220> FEATURE:
<223> OTHER INFORMATION: IL1 beta reverse primer

<400> SEQUENCE: 4
cggagattcg tagctggatg                                         20

<210> SEQ ID NO 5
<211> LENGTH: 20
<212> TYPE: DNA
<213> ORGANISM: Artificial Sequence
<220> FEATURE:
<223> OTHER INFORMATION: IL2 forward primer

<400> SEQUENCE: 5
aacctctgga ggaagtgcta                                         20

<210> SEQ ID NO 6
<211> LENGTH: 21
<212> TYPE: DNA
<213> ORGANISM: Artificial Sequence
<220> FEATURE:
<223> OTHER INFORMATION: IL2 reverse primer

<400> SEQUENCE: 6
aatggttgct gtctcatcag c                                       21

<210> SEQ ID NO 7
<211> LENGTH: 20
<212> TYPE: DNA
<213> ORGANISM: Artificial Sequence
<220> FEATURE:
<223> OTHER INFORMATION: IL3 forward primer

<400> SEQUENCE: 7
cacgcgacat ccaatccata                                         20

<210> SEQ ID NO 8
<211> LENGTH: 20
<212> TYPE: DNA

```
<213> ORGANISM: Artificial Sequence
<220> FEATURE:
<223> OTHER INFORMATION: IL3 reverse primer

<400> SEQUENCE: 8
tcaaagtcgt ctgttgagcc                                               20

<210> SEQ ID NO 9
<211> LENGTH: 20
<212> TYPE: DNA
<213> ORGANISM: Artificial Sequence
<220> FEATURE:
<223> OTHER INFORMATION: IL4 forward primer

<400> SEQUENCE: 9
ccgagttgac cgtaacagac                                               20

<210> SEQ ID NO 10
<211> LENGTH: 21
<212> TYPE: DNA
<213> ORGANISM: Artificial Sequence
<220> FEATURE:
<223> OTHER INFORMATION: IL4 reverse primer

<400> SEQUENCE: 10
gttctctctg ggctttgtag g                                             21

<210> SEQ ID NO 11
<211> LENGTH: 20
<212> TYPE: DNA
<213> ORGANISM: Artificial Sequence
<220> FEATURE:
<223> OTHER INFORMATION: TNF alpha forward primer

<400> SEQUENCE: 11
atcatcttct cgaaccccga                                               20

<210> SEQ ID NO 12
<211> LENGTH: 20
<212> TYPE: DNA
<213> ORGANISM: Artificial Sequence
<220> FEATURE:
<223> OTHER INFORMATION: TNF alpha reverse primer

<400> SEQUENCE: 12
gttatctctc agctccacgc                                               20

<210> SEQ ID NO 13
<211> LENGTH: 20
<212> TYPE: DNA
<213> ORGANISM: Artificial Sequence
<220> FEATURE:
<223> OTHER INFORMATION: IL10 forward primer

<400> SEQUENCE: 13
cctgcctaac atgcttcgag                                               20

<210> SEQ ID NO 14
<211> LENGTH: 20
<212> TYPE: DNA
<213> ORGANISM: Artificial Sequence
<220> FEATURE:
<223> OTHER INFORMATION: IL10 reverse primer

<400> SEQUENCE: 14
gtcttggttc tcagcttggg                                               20
```

```
<210> SEQ ID NO 15
<211> LENGTH: 20
<212> TYPE: DNA
<213> ORGANISM: Artificial Sequence
<220> FEATURE:
<223> OTHER INFORMATION: TGF beta forward primer

<400> SEQUENCE: 15
gactcgccag agtggttatc                                           20

<210> SEQ ID NO 16
<211> LENGTH: 20
<212> TYPE: DNA
<213> ORGANISM: Artificial Sequence
<220> FEATURE:
<223> OTHER INFORMATION: TGF beta reverse primer

<400> SEQUENCE: 16
ggtagtgaac ccgttgatgt                                           20

<210> SEQ ID NO 17
<211> LENGTH: 19
<212> TYPE: DNA
<213> ORGANISM: Artificial Sequence
<220> FEATURE:
<223> OTHER INFORMATION: Beta actin forward primer

<400> SEQUENCE: 17
aactaccttc aactccatc                                            19

<210> SEQ ID NO 18
<211> LENGTH: 18
<212> TYPE: DNA
<213> ORGANISM: Artificial Sequence
<220> FEATURE:
<223> OTHER INFORMATION: Beta actin reverse primer

<400> SEQUENCE: 18
cttgctgatc cacatctg                                             18
```